(12) United States Patent
Hoshino et al.

(10) Patent No.: US 10,005,718 B2
(45) Date of Patent: Jun. 26, 2018

(54) CATALYST, AND METHOD FOR PRODUCING OXIDATION PRODUCT

(71) Applicant: Sumitomo Chemical Company, Limited, Tokyo (JP)

(72) Inventors: Masahiro Hoshino, Oita (JP); Yuta Kikuchi, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days. days.

(21) Appl. No.: 15/116,699

(22) PCT Filed: Feb. 4, 2015

(86) PCT No.: PCT/JP2015/053138
§ 371 (c)(1),
(2) Date: Aug. 4, 2016

(87) PCT Pub. No.: WO2015/119167
PCT Pub. Date: Aug. 13, 2015

(65) Prior Publication Data
US 2016/0347707 A1     Dec. 1, 2016

(30) Foreign Application Priority Data

Feb. 7, 2014    (JP) .................................. 2014-021974

(51) Int. Cl.

| | |
|---|---|
| C07C 231/10 | (2006.01) |
| B01J 31/02 | (2006.01) |
| C07C 249/04 | (2006.01) |
| C07C 251/44 | (2006.01) |
| B01J 21/06 | (2006.01) |
| B01J 21/16 | (2006.01) |
| B01J 23/46 | (2006.01) |
| B01J 27/02 | (2006.01) |

(52) U.S. Cl.
CPC ........... *C07C 231/10* (2013.01); *B01J 21/063* (2013.01); *B01J 21/16* (2013.01); *B01J 23/462* (2013.01); *B01J 27/02* (2013.01); *B01J 31/02* (2013.01); *B01J 31/0235* (2013.01); *B01J 31/0247* (2013.01); *C07C 249/04* (2013.01); *C07C 251/44* (2013.01); *C07C 2601/14* (2017.05); *Y02P 20/582* (2015.11)

(58) Field of Classification Search
None
See application file for complete search history.

(56) References Cited

U.S. PATENT DOCUMENTS

| 4,156,783 A | 5/1979 | Lyons et al. |
| 2007/0078284 A1 | 4/2007 | Tanielyan et al. |
| 2010/0069670 A1 | 3/2010 | Yamamoto et al. |
| 2015/0353478 A1 | 12/2015 | Hoshino et al. |

FOREIGN PATENT DOCUMENTS

| CN | 103204514 A | 7/2013 |
| EP | 2617680 A1 | 7/2013 |
| EP | 2980065 A1 | 2/2016 |
| JP | S6445339 A | 2/1989 |
| JP | 2002249450 A | 9/2002 |
| JP | 2007-525522 A | 9/2007 |
| JP | 2013147356 A | 8/2013 |
| WO | 199617030 A1 | 6/1996 |
| WO | 2005009613 A1 | 2/2005 |
| WO | 2005082825 A1 | 9/2005 |

OTHER PUBLICATIONS

Standard electrode potential chart: https://en.wikipedia.org/wiki/Standard_electrode_potential_(data_page), downloaded on Jul. 9, 2017, p. 1-12.*
Han ("A review of the direct oxidation of methane to methanol" Chinese Journal of Catalysis, vol. 37, 2016, p. 1206-1215) (Year: 2016).*
Mesfer ("Catalytic Conversion of Benzene to Phenol" Russian Journal of Applied Chemistry, vol. 89, No. 11, 2016, p. 1869-1878) (Year: 2016).*
Mohan ("Regioselective alpha-bromination of aralkyl ketones using N-Bromosuccinimide in the presence of Montmorillonite K-10 clay: A simple and Efficient Method" Synthetic Communications, vol. 43, 2013, p. 2603-2614) (Year: 2013).*
Chiba ("Product Class 15: Oximes", Science of Synthesis, Knowledge Updates, 4, 2011, p. 445-499), particularly p. 450-452 which discusses known catalysts for the oxidation of amines to oximes) (Year: 2011).*
Sakaue et al., "Oxidation of Aliphatic and Aromatic Amines with Hydrogen Peroxide Catalyzed by Peroxoheteropoly Dxometalates", Chemistry Letters, pp. 289-292 (1992).

(Continued)

*Primary Examiner* — Jafar Parsa
*Assistant Examiner* — Amy C Bonaparte
(74) *Attorney, Agent, or Firm* — Panitch Schwarze Belisario & Nadel LLP

(57) ABSTRACT

A novel catalyst is provided which enables efficient production of an oxidation product by using an oxygen-induced oxidation reaction of an organic substrate. A novel method of using the catalyst enables efficient manufacturing of the oxidation product by oxidizing the organic substrate using oxygen. A catalyst used in the oxidation reaction of the organic substrate using oxygen contains compound (A), compounds (A) and (B), compounds (A) and (C), compounds (B) and (C), or compounds (A) and (B) and (C). A method for manufacturing the oxidation product using the catalyst involves bringing the organic substrate into contact with oxygen. Compound (A) is an inorganic peroxo acid, a salt of an inorganic peroxo acid, and/or N-halogenated succinimide, compound (B) is a nitroxide and/or a peroxide, and compound (C) is layered silicate.

5 Claims, No Drawings

(56) References Cited

OTHER PUBLICATIONS

Int'l Search Report dated Apr. 28, 2015 in Int'l Application No. PCT/JP2015/053138.
Int'l Preliminary Report dated Apr. 28, 2015 in Int'l Application No. PCT/JP2015/053138.
Office Action and Search Report dated Jun. 21, 2017 in CN Application No. 201580007476.0.
Partial Supplementary European Search Report dated Sep. 25, 2017 in EP Application No. 15747081.6.
Fields et al., "Surface-Mediated Reactions", Journ. of Organic Chemistry, vol. 65, No. 19, pp. 5937-5941 (Sep. 2000).
Travis et al., "Facile Oxidation of Aldehydes to Acids and Esters with Oxone", Organic Letters, vol. 5, No. 7, pp. 1031-1034 (Apr. 2003).
Gonzalez-Nunez et al., "Baeyer-Villiger Oxidation with Potassium Peroxomonosulfate Supported on Acidic Silica Gel", Journ. of Organic Chemistry, vol. 70, No. 26, pp. 10879-10882 (Dec. 2005).
De Luca et al., "Beckmann Rearrangement of Oximes Under Very Mild Conditions" J. Org. Chem, vol. 67, pp. 6272-6274, 2002.
Extended European Search Report dated Apr. 19, 2018 issued in EP 15747081.6.

\* cited by examiner

CATALYST, AND METHOD FOR PRODUCING OXIDATION PRODUCT

CROSS-REFERENCE TO RELATED APPLICATION

This application is a Section 371 of International Application No. PCT/JP2015/053138, filed Feb. 4, 2015, which was published in the Japanese language on Aug. 13, 2015, under International Publication No. WO 2015/119167 A1, and the disclosure of which is incorporated herein by reference.

TECHNICAL FIELD

The present patent application claims the priority under the Paris Convention based on Japanese patent application No. 2014-21974, the entirety of which is incorporated herein by reference.

The present invention relates to a catalyst, and a method for producing an oxidation product.

BACKGROUND ART

In a reaction of oxidizing an organic substrate, such as an amine, a hydrocarbon, an aldehyde, a ketone, or an alcohol with oxygen, use of a variety of catalysts has hitherto been studied, and reported. As such a catalyst, for example, Patent Document 1 describes a catalyst comprising a hydrazyl radical or a hydrazine compound and a transition metal compound, the catalyst being used in a reaction of oxidizing an amine with oxygen, and Patent Document 2 describes a catalyst comprising an N-hydroxy cyclic imide and a transition metal compound, the catalyst being used in a reaction of oxidizing a hydrocarbon, an aldehyde, a ketone or an alcohol with oxygen.

PRIOR ART DOCUMENT

Patent Documents

Patent Document 1: WO 2005/009613 A
Patent Document 2: JP 2002-249450 A

SUMMARY OF THE INVENTION

Problems to be Solved by the Invention

An object of the present invention is to provide a new catalyst the use of which in an oxidation reaction of an organic substrate with oxygen makes it possible to efficiently obtain an oxidation product. Another object of the invention is to provide a novel method in which an organic substrate is oxidized with oxygen to efficiently produce an oxidation product.

Solutions to the Problems

The present inventors have intensively studied so as to achieve the above object, and thus the present invention has been completed.

The present invention includes the following embodiments.

(1) A catalyst for use in an oxidation reaction of an organic substrate with oxygen, the catalyst comprising the following compound (A), the following compounds (A) and (B), the following compounds (A) and (C), the following compounds (B) and (C), or the following compounds (A), (B) and (C):

Compound (A): at least one compound selected from the group consisting of an inorganic peroxo acid, a salt of an inorganic peroxo acid, and N-halogenated succinimide;

Compound (B): at least one compound selected from the group consisting of a nitroxide and a peroxide;

Compound (C): a layered silicate.

(2) The catalyst according to the above (1), wherein the layered silicate is smectite.

(3) The catalyst according to the above (1) or (2), wherein the layered silicate contains at least one selected from the group consisting of hydrogen ion, ammonium ion, quaternary ammonium ions, cations of Group 4 metal elements, cations of Group 5 metal elements, cations of Group 6 metal elements, germanium ions, oxides of positively charged Group 4 metal elements, oxides of positively charged Group 5 metal elements, oxides of positively charged Group 6 metal elements, and positively charged germanium oxides.

(4) The catalyst according to any one of the above (1) to (3), wherein the inorganic peroxo acid is at least one compound selected from the group consisting of a peroxomonosulfuric acid and a peroxodisulfuric acid, and the salt of the inorganic peroxo acid is at least one compound selected from the group consisting of a peroxomonosulfate and a peroxodisulfate.

(5) The catalyst according to any one of the above (1) to (4), wherein the nitroxide is at least one compound selected from the group consisting of 2,2,6,6-tetramethylpiperidin-1-oxyl and 4-substituted-2,2,6,6-tetramethylpiperidin-1-oxyl.

(6) The catalyst according to any one of the above (1) to (5), wherein the peroxide is benzoyl peroxide.

(7) The catalyst according to any one of the above (1) to (6), wherein the organic substrate is an amine represented by the following formula (I) [hereinafter sometimes referred to as the amine compound (I)]:

[Chemical Formula 1]

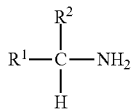

(I)

wherein $R^1$ and $R^2$ each independently represents a hydrogen atom, an optionally substituted hydrocarbon group, or an optionally substituted heterocyclic group, provided that not both $R^1$ and $R^2$ are hydrogen atoms, or $R^1$ and $R^2$, taken together with the carbon atom to which $R^1$ and $R^2$ are attached, form an optionally substituted alicyclic hydrocarbon group having 3 to 12 carbon atoms.

(8) A method for producing an oxidation product, comprising bringing an organic substrate into contact with oxygen in the presence of the catalyst according to any one of the above (1) to (6).

(9) The method according to the above (8), wherein the organic substrate is an amine compound (I), and the oxidation product is an oxime represented by the following formula (II) [hereinafter sometimes referred to as the oxime compound (II)]:

[Chemical Formula 2]

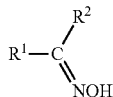
(II)

wherein $R^1$ and $R^2$ are each the same as defined above.

(10) A method for producing an amide represented by the following formula (III) [hereinafter sometimes referred to as the amide compound (III)]:

[Chemical Formula 3]

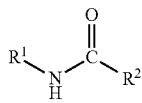
(III)

wherein $R^1$ and $R^2$ each independently represents a hydrogen atom, an optionally substituted hydrocarbon group, or an optionally substituted heterocyclic group (provided that $R^1$ and $R^2$ are not simultaneously hydrogen atoms), or $R^1$ and $R^2$, taken together with the nitrogen atom to which $R^1$ is attached, and the carbon atom to which $R^2$ is attached, form an optionally substituted alicyclic hydrocarbon group having 3 to 12 carbon atoms, the method comprising allowing the oxime compound (II) produced by the method according to the above (9) to undergo a Beckmann rearrangement reaction.

Effects of the Invention

According to the present invention, there can be provided a new catalyst the use of which in an oxidation reaction of an organic substrate with oxygen makes it possible to efficiently obtain an oxidation product. In addition, there can be provided a novel method in which an organic substrate is oxidized with oxygen to efficiently produce an oxidation product.

MODE FOR CARRYING OUT THE INVENTION

The present invention will be described in detail below. The catalyst of the present invention is a catalyst used in an oxidation reaction of an organic substrate with oxygen, and comprises the following compound (A), the following compounds (A) and (B), the following compounds (A) and (C), the following compounds (B) and (C), or the following compounds (A), (B) and (C):
Compound (A): at least one compound selected from the group consisting of an inorganic peroxo acid, a salt of an inorganic peroxo acid, and N-halogenated succinimide;
Compound (B): at least one compound selected from the group consisting of a nitroxide and a peroxide;
Compound (C): a layered silicate.

The catalyst of the present invention comprises at least one compound selected from the group consisting of an inorganic peroxo acid, a salt of an inorganic peroxo acid, and N-halogenated succinimide; or comprises at least one compound selected from the group consisting of an inorganic peroxo acid, a salt of an inorganic peroxo acid, and N-halogenated succinimide, and at least one selected from the group consisting of a nitroxide and a peroxides; or comprises at least one compound selected from the group consisting of an inorganic peroxo acid, a salt of an inorganic peroxo acid, and N-halogenated succinimide, and a layered silicate; or comprises at least one compound selected from the group consisting of a nitroxide and a peroxide, and a layered silicate; or comprises at least one compound selected from the group consisting of an inorganic peroxo acid, a salt of an inorganic peroxo acid, and N-halogenated succinimide, at least one compound selected from the group consisting of a nitroxide and a peroxide, and a layered silicate.

Examples of the organic substrate include an amine, a hydrocarbon, an aldehyde, a ketone, and an alcohol and, if necessary, two or more thereof can also be used. Of the organic substrates, the catalyst of the present invention is advantageously adopted when an amine is used.

Examples of the amine include the amine compound (I). In the formulas (I), (II) and (III), when $R^1$ and $R^2$ each independently represents a hydrogen atom, an optionally substituted hydrocarbon group, or an optionally substituted heterocyclic group, not both $R^1$ and $R^2$ are hydrogen atoms. Herein, "optionally substituted" refers to a hydrocarbon group or a heterocyclic group in which hydrogen atoms in a hydrocarbon group or a heterocyclic group may be partially or entirely substituted with another substituent. In $R^1$ and $R^2$, examples of the hydrocarbon group include an alkyl group, an alkenyl group, an alkynyl group, a cycloalkyl group, a cycloalkenyl group, and an aryl group.

The alkyl group is preferably an alkyl group having 1 to 24 carbon atoms, and examples thereof include a methyl group, an ethyl group, a propyl group, an isopropyl group, a butyl group, an isobutyl group, an s-butyl group, a t-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, an eicosyl group, a henicosyl group, a heneicosyl group, a docosyl group, a tricosyl group, and a tetracosyl group.

The alkenyl group is preferably an alkenyl group having 2 to 24 carbon atoms, and examples thereof include a vinyl group, an allyl group, a 2-methylallyl group, an isopropenyl group, a 1-propenyl group, a 1-butenyl group, a 2-butenyl group, a 3-butenyl group, a 1-methyl-1-propenyl group, a 1-methyl-2-propenyl group, a 2-methyl-1-propenyl group, a 2-methyl-2-propenyl group, a 1-pentenyl group, a 2-pentenyl group, a 3-pentenyl group, a 4-pentenyl group, a 1-methyl-1-butenyl group, a 2-methyl-1-butenyl group, a 3-methyl-1-butenyl group, a 1-methyl-2-butenyl group, a 2-methyl-2-butenyl group, a 3-methyl-2-butenyl group, a 1-hexenyl group, a 2-hexenyl group, a 3-hexenyl group, a 4-hexenyl group, a 5-hexenyl group, a 1-methyl-1-pentenyl group, a 2-methyl-1-pentenyl group, a 4-methyl-3-pentenyl group, a 2-ethyl-1-butenyl group, a 2-heptenyl group, a 2-octenyl group, a 2-nonenyl group, a 2-decenyl group, a 2-undecenyl group, a 2-dodecenyl group, a 2-tridecenyl group, a 2-tetradecenyl group, a 2-pentadecenyl group, a 2-hexadecenyl group, a 2-heptadecenyl group, a 2-octadecenyl group, a 2-nonadecenyl group, a 2-icosenyl group, a 2-eicosenyl group, a 2-henicosenyl group, a 2-heneicosenyl group, a 2-dococenyl group, a 2-tricosenyl group, and a 2-tetracosenyl group.

The alkynyl group is preferably an alkynyl group having 2 to 24 carbon atoms, and examples thereof include an ethynyl group, a 1-propynyl group, a 2-propynyl group, a 1-butynyl group, a 2-butynyl group, a 3-butynyl group, a 1-methyl-2-propynyl group, a 1-pentynyl group, a 2-pentynyl group, a 3-pentynyl group, a 4-pentynyl group, a 1-methyl-3-butynyl group, a 2-methyl-3-butynyl group, a 1-hexynyl group, a 2-hexynyl group, a 3-hexynyl group, a 4-hexynyl group, a 5-hexynyl group, a 2-heptynyl group, a 2-octynyl group, a 2-nonynyl group, a 2-decynyl group, a 2-undecynyl group, a 2-dodecynyl group, a 2-tridecynyl group, a 2-tetradecynyl group, a 2-pentadecynyl group, a 2-hexadecynyl group, a 2-heptadecynyl group, a 2-octadecynyl group, a 2-nonadecynyl group, a 2-icosynyl group, a 2-eicosynyl group, a 2-henicosynyl group, a 2-heneicosynyl group, a 2-docosynyl group, a 2-tricosynyl group, and a 2-tetracosynyl group.

The cycloalkyl group is preferably a cycloalkyl group having 3 to 8 carbon atoms, and examples thereof include a cyclopropyl group, a cyclobutyl group, a cyclopentyl group, a cyclohexyl group, a cycloheptyl group, and a cyclooctyl group.

The cycloalkenyl group is preferably a cycloalkenyl group having 3 to 8 carbon atoms, and examples thereof include a cyclopropenyl group, a cyclobutenyl group, a cyclopentenyl group, a cyclohexenyl group, a cycloheptenyl group, and a cyclooctenyl group.

Examples of the aryl group include a phenyl group, a naphthyl group, an anthracenyl group, a phenanthryl group, a tolyl group, and a xylyl group.

In $R^1$ and $R^2$, the hydrocarbon group may be optionally substituted. When the hydrocarbon group is an alkyl group, an alkenyl group, or an alkynyl group, examples of the substituent thereof include halogen atoms such as fluorine, chlorine, and bromine atoms; cycloalkyl groups having 3 to 6 carbon atoms, such as a cyclopropyl group, a 1-methylcyclopropyl group, a cyclobutyl group, a cyclopentyl group, a 1-methylcyclopentyl group, and a cyclohexyl group; alkoxy groups having 1 to 4 carbon atoms, such as a methoxy group, an ethoxy group, a propoxy group, an isopropoxy group, a butoxy group, an s-butoxy group, an isobutoxy group, and a t-butoxy group; thioalkoxy group having 1 to 4 carbon atoms, such as a thiomethoxy group, a thioethoxy group, a thiopropoxy group, and a thiobutoxy group; alkenyloxy groups having 3 to 4 carbon atoms, such as an allyloxy group, a 2-propenyloxy group, a 2-butenyloxy group, and a 2-methyl-3-propenyloxy group; aralkyloxy groups having 7 to 20 carbon atoms; aryl groups having 6 to 18 carbon atoms, such as a phenyl group, a naphthyl group, an anthracenyl group, and a phenanthryl group; aryloxy groups such as a phenyloxy group and a naphthyloxy group; alkanoyl groups having 2 to 7 carbon atoms; aryloyl groups having 7 to 19 carbon atoms; and alkoxycarbonyl groups having 1 to 6 carbon atoms. When the hydrocarbon group is an alkyl group, examples of the alkyl group substituted with an aryl group having 6 to 18 carbon atoms include aralkyl groups such as a benzyl group, a phenethyl group, a 3-phenylpropyl group, a benzhydryl group, a trityl group, a triphenylethyl group, a (1-naphthyl)methyl group, and a (2-naphthyl)methyl group.

In $R^1$ and $R^2$, when the hydrocarbon group is a cycloalkyl group, a cycloalkenyl group, or an aryl group, examples of the substituent include the above-mentioned halogen atoms; cycloalkyl groups having 3 to 6 carbon atoms; alkoxy groups having 1 to 4 carbon atoms; thioalkoxy groups having 1 to 4 carbon atoms; alkenyloxy groups having 3 to 4 carbon atoms; aralkyloxy groups having 7 to 20 carbon atoms; aryl groups having 6 to 18 carbon atoms; aryloxy groups; alkanoyl groups having 2 to 7 carbon atoms; aryloyl groups having 7 to 19 carbon atoms; alkoxycarbonyl groups having 1 to 6 carbon atoms; alkyl groups having 1 to 6 carbon atoms, such as a methyl group, an ethyl group, a propyl group, an isopropyl group, a butyl group, an isobutyl group, an s-butyl group, a t-butyl group, a pentyl group, and a hexyl group; alkenyl groups having 2 to 6 carbon atoms, such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group; and aralkyl groups having 7 to 20 carbon atoms, such as a benzyl group, a phenethyl group, and a naphthylmethyl group.

In $R^1$ and $R^2$, examples of the heterocyclic group include a heteroaryl group and a heteroaralkyl group. The heteroaryl group is preferably a heteroaryl group having 3 to 9 carbon atoms, and examples thereof include a pyridyl group, a quinonyl group, a pyrrolyl group, an imidazolyl group, a furyl group, an indolyl group, a thienyl group, and an oxazolyl group. The heteroaralkyl group is preferably a heteroaralkyl group having 5 to 10 carbon atoms, and examples thereof include a pyridylmethyl group, a quinolylmethyl group, an indolylmethyl group, a furylmethyl group, and a pyrrolylmethyl group.

In $R^1$ and $R^2$, the heterocyclic group may be optionally substituted. Examples of the substituent in the heterocyclic group include the above-mentioned halogen atoms; cycloalkyl groups having 3 to 6 carbon atoms; alkoxy groups having 1 to 4 carbon atoms; thioalkoxy groups having 1 to 4 carbon atoms; alkenyloxy groups having 3 to 4 carbon atoms; aralkyloxy groups having 7 to 20 carbon atoms; aryl groups having 6 to 18 carbon atoms; aryloxy groups; alkanoyl groups having 2 to 7 carbon atoms; aryloyl groups having 7 to 19 carbon atoms; alkoxycarbonyl groups having 1 to 6 carbon atoms; alkyl groups having 1 to 6 carbon atoms; alkenyl groups having 2 to 6 carbon atoms; and aralkyl groups having 7 to 20 carbon atoms.

In the formula (I), when $R^1$ and $R^2$ each independently represent a hydrogen atom or an optionally substituted hydrocarbon group, examples of the amine compound (I) include methylamine, ethylamine, n-propylamine, isopropylamine, n-butylamine, isobutylamine, s-butylamine, t-butylamine, pentylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, nonadecylamine, icosylamine, eicosylamine, henicosylamine, heneicosylamine, docosylamine, tricosylamine, tetracosylamine, 1-methylbutylamine, 2-methylbutylamine, cyclopropylmethylamine, cyclohexylmethylamine, benzylamine, 2-methylbenzylamine, 4-methylbenzylamine, 1-phenylethylamine, 2-phenylethylamine, 3-aminomethylpyridine, 1-(4-chlorophenyl)ethylamine, 2-(2-chlorophenyl)ethylamine, 1-(3-methoxyphenyl)ethylamine, 1-(4-methoxyphenyl)ethylamine, 2-(2-methoxyphenyl)ethylamine, 2-(3-methoxyphenyl)ethylamine, 2-(4-methoxyphenyl)ethylamine, 1-[3-(trifluoromethyl)phenyl]ethylamine, 1-(1-naphthyl)ethylamine, 1-(2-naphthyl)ethylamine, 1-phenylpropylamine, and 3-phenylpropylamine.

In the formulas (I) and (II), when $R^1$ and $R^2$ are taken together with the carbon atom to which $R^1$ and $R^2$ are attached to form an optionally substituted alicyclic hydrocarbon group having 3 to 12 carbon atoms, the number of carbon atoms is preferably 6 to 12. Here, the alicyclic hydrocarbon group having 3 to 12 carbon atoms refers to an alicyclic hydrocarbon group of 3- to 12-membered ring, and "optionally substituted" refers to an alicyclic hydrocarbon group in which hydrogen atoms in a methylene group in the alicyclic hydrocarbon group may be partially or entirely substituted with another substituent. When substituted with another substituent, the number of carbon atoms of the substituent is not included in the above-mentioned number of carbon atoms. Examples of the substituent in the alicyclic hydrocarbon group having 3 to 12 carbon atoms include the above-mentioned halogen atoms, cycloalkyl groups having 3 to 6 carbon atoms, alkoxy groups having 1 to 4 carbon atoms, thioalkoxy groups having 1 to 4 carbon atoms, alkenyloxy groups having 3 to 4 carbon atoms, aralkyloxy groups having 7 to 20 carbon atoms, aryl groups having 6 to 18 carbon atoms, aryloxy groups, alkanoyl groups having 2 to 7 carbon atoms, aryloyl groups having 7 to 19 carbon atoms, alkoxycarbonyl groups having 1 to 6 carbon atoms, the above-mentioned alkyl groups having 1 to 6 carbon atoms, alkenyl groups having 2 to 6 carbon atoms, and aralkyl groups having 7 to 20 carbon atoms.

In the formulas (I) and (II), when $R^1$ and $R^2$ are taken together with the carbon atom to which $R^1$ and $R^2$ are attached to form an optionally substituted alicyclic hydrocarbon group having 3 to 12 carbon atoms, examples of the amine compound (I) include cyclohexylamine, cyclooctylamine, cyclopentylamine, cycloheptylamine, cyclododecylamine, 2-methylcyclohexylamine, and 4-methylcyclohexylamine.

When cyclohexylamine, of amine compounds (I), is used as a starting material, it is advantageous to employ the catalyst of the present invention in that cyclohexanone oxime is obtained in high selectivity. Cyclohexylamine may be obtained, for example, by hydrogenating aniline, nitrobenzene, nitrocyclohexane, or the like, or may be obtained by an amination reaction of cyclohexene or cyclohexanol with ammonia.

Examples of the hydrocarbon used as the organic substrate include saturated aliphatic acyclic hydrocarbons, such as propane, butane, isobutane, pentane, hexane, octane, and decane; saturated aliphatic cyclic hydrocarbons, such as cyclobutane, cyclopentane, cyclohexane, methylcyclohexane, cycloheptane, cyclooctane, cyclononane, and cyclodecane; unsaturated aliphatic acyclic hydrocarbons, such as butene, isobutylene, butadiene, and isoprene; unsaturated aliphatic cyclic hydrocarbons, such as cyclopropene, cyclobutene, cyclopentene, cyclohexene, methylcyclohexene, cycloheptene, cyclooctene, cyclononene, and cyclodecene; aromatic hydrocarbons, such as toluene, xylene, cumene, cymene, diisopropylbenzene, tetralin, and indane.

Examples of the aldehyde used as the organic substrate include propionaldehyde, butylaldehyde, valeraldehyde, 3-(methylthio)propionaldehyde, 2-ethylhexanal, isobutylaldehyde, furfural, crotonaldehyde, acrolein, methacrolein, benzaldehyde, substituted benzaldehyde, phenylacetaldehyde, 2, 4-dihydroxyphenylacetaldehyde, glyoxalic acid, and α-acetoxypropionaldehyde.

Examples of the alcohol used as the organic substrate include monohydric or polyhydric, saturated aliphatic acyclic alcohols, saturated aliphatic cyclic alcohols, unsaturated aliphatic acyclic alcohols, unsaturated aliphatic cyclic alcohols, and aromatic alcohols, in which a methyl group, a methylene group or a methylidyne group in the hydrocarbons used as the organic substrate is converted to a hydroxymethyl group, a hydroxymethylene group or a hydroxymethylidyne group, respectively.

Examples of the ketone used as the organic substrate include methyl ethyl ketone, methyl isobutyl ketone, and cyclohexanone.

There is no particular limitation on the inorganic peroxo acid, as long as it is an inorganic oxo acid having an —O—O— bond, and examples thereof include peroxomonosulfuric acid, peroxodisulfuric acid, peroxomonocarbonic acid, peroxodicarbonic acid, peroxomonophosphoric acid, peroxodiphosphoric acid, peroxoboric acid, and peroxonitric acid and, if necessary, two or more thereof can also be used. Examples of a salt of the inorganic peroxo acid include alkali metal salts (sodium salts, potassium salts, lithium salts, etc.), alkaline earth metal salts (magnesium salts, calcium salts, barium salts, etc.), ammonium salts, and quaternary ammonium salts (tetrabutylammonium salts, etc.) of the inorganic peroxo acid and, if necessary, two or more thereof can also be used. In the present invention, it is preferred to bring the amine compound (I) into contact with oxygen in the presence of at least one compound selected from the group consisting of peroxomonosulfuric acid, peroxodisulfuric acid, peroxomonosulfate and peroxodisulfate. The peroxomonosulfate and the peroxodisulfate are, of the inorganic peroxo acids, preferably a potassium salt, a sodium salt, an ammonium salt, and a quaternary ammonium salt, and more preferably a potassium salt, a sodium salt, and an ammonium salt. When potassium peroxomonosulfate is used as the salt of the inorganic peroxo acid, it may be used in the form of OXONE (registered trademark of Du Pont, a mixture of potassium peroxomonosulfate, potassium sulfate and potassium hydrogen sulfate). Since the inorganic peroxo acid and the salt of the inorganic peroxo acid are inexpensive and industrially easily available, an oxidation product can be industrially produced advantageously by using the inorganic peroxo acid and/or the salt of the inorganic peroxo acid. By using the inorganic peroxo acid and/or the salt of the inorganic peroxo acid, an oxidation product can also be produced with good selectivity.

Examples of the N-halogenated succinimide include N-bromosuccinimide, N-chlorosuccinimide, and N-iodosuccinimide and, if necessary, two or more thereof can also be used. Since the N-halogenated succinimide is inexpensive and industrially easily available, an oxidation product can be industrially produced advantageously by using the N-halogenated succinimide. By using the N-halogenated succinimide, an oxidation product can also be produced with good yield.

Examples of the nitroxide include 2,2,6,6-tetramethylpiperidin-1-oxyl and 4-substituted-2,2,6,6-tetramethylpiperidin-1-oxyl which are inexpensive and industrially easily available and, if necessary, both of 2,2,6,6-tetramethylpiperidin-1-oxyl and 4-substituted-2,2,6,6-tetramethylpiperidin-1-oxyl can also be used. Examples of the 4-substituted-2,2,6,6-tetramethylpiperidin-1-oxyl include 4-hydroxy-2,2,6,6-tetramethylpiperidin-1-oxyl, 4-oxo-2,2,6,6-tetramethylpiperidin-1-oxyl, 4-methoxy-2,2,6,6-tetramethylpiperidin-1-oxyl, 4-ethoxy-2,2,6,6-tetramethylpiperidin-1-oxyl, 4-phenoxy-2,2,6,6-tetramethylpiperidin-1-oxyl, 4-amino-2,2,6,6-tetramethylpiperidin-1-oxyl, 4-carboxy-2,2,6,6-tetramethylpiperidin-1-oxyl, 4-cyano-2,2,6,6-tetramethylpiperidin-1-oxyl, and 4-carbamoyl-2,2,6,6-tetramethylpiperidin-1-oxyl and, if necessary, two or more thereof can also be used. By using at least one compound selected from the group consisting of 2,2,6,6-tetramethylpiperidin-1-oxyl and 4-substituted-2,2,6,6-tetramethylpiperidin-1-oxyl, an oxidation product can be industrially produced advantageously with good yield.

Examples of the peroxide include hydrogen peroxide and an organic peroxide. Examples of the organic peroxide include diacylperoxides, such as benzoyl peroxide, diisobutyryl peroxide, di(3,5,5-trimethylhexanoyl) peroxide, dilauroyl peroxide, disuccinic acid peroxide, di(4-methylbenzoyl) peroxide, and diacetyl peroxide; hydroperoxides, such as t-butyl hydroperoxide, cumene hydroperoxide, 1,1-dimethylpropyl hydroperoxide, cyclohexyl hydroperoxide, diisopropylbenzene hydroperoxide, p-menthane hydroperoxide, and 1,1,3,3-tetramethylbutyl hydroperoxide; dialkyl peroxides, such as t-butylcumyl peroxide, di-t-butyl peroxide, di-t-hexyl peroxide, dicumyl peroxide, α,α'-di(t-butylperoxy)diisopropylbenzene, 2,5-dimethyl-2,5-di(t-butylperoxy)hexane, and 2,5-dimethyl-2,5-bis(t-butylperoxy)hexyne-3; peroxy esters, such as cumylperoxy neodecanoate, 1,1,3,3-tetramethylbutylperoxy neodecanoate, t-hexylperoxy neodecanoate, t-butylperoxy neodecanoate, t-butylperoxy neoheptanoate, t-hexylperoxy pivalate, t-butylperoxy pivalate, 2,5-dimethyl-2,5-di(2-ethylhexanoylperoxy)hexane, 1,1,3,3-tetramethylbutylperoxy-2-ethyl hexanoate, t-hexylperoxy-2-ethyl hexanoate, t-butylperoxy-2-ethyl hexanoate, t-butylperoxy laurate, t-butylperoxy-3,5,5-trimethyl hexanoate, t-hexylperoxyisopropyl monocarbonate, t-butylperoxy-2-ethylhexyl monocarbonate, 2,5-dimethyl-2,5-di(benzoylperoxy)hexane, t-butyl peroxyacetate, t-hexyl peroxybenzoate, and t-butyl peroxybenzoate; peroxydicarbonates, such as diisopropyl peroxydicarbonate, di-n-propyl peroxydicarbonate, bis(4-t-butylcyclohexyl) peroxydicarbonate, di-2-ethylhexyl peroxydicarbonate, and di-sec-butyl peroxydicarbonate; ketone peroxides, such as methyl ethyl ketone peroxide. Of the organic peroxides, diacyl peroxides are preferable. Among diacyl peroxides, benzoyl peroxide is preferable.

The layered silicate may be either a natural product or an artificially synthesized synthetic product, or may be a mixture thereof. Examples of the method for synthesizing a synthetic product include a hydrothermal synthesis reaction method, a solid phase reaction method, and a melt synthesis method. Examples of the layered silicate include smectites such as montmorillonite, saponite, beidellite, nontronite, sauconite, stevensite, hectorite, volkonskoite, and swinefordite; vermiculites; micas such as muscovite, phlogopite, annite, eastonite, siderophyllite tetra-ferri-annite, polylithionite, celadonite, ferro-celadonite, ferro-aluminoceladonite, aluminoceladonite, tobelite, and paragonite; brittle micas such as clintonite, bityite, and margarite; chlorites such as clinochlore, chamosite, pennantite, nimite, baileychlore, cookeite, and sudoite; talc; pyrophyllites; kaolinites such as kaolinite, dickite, nacrite, halloysite, amesite, berthierine, cronstedtite, nepouite, kellyite, fraiponite, and brindleyite; and serpentines such as antigorite, chrysotile, and lizardite and, if necessary, two or more layered silicates thereof can also be used. Of these layered silicates smectite is preferable in view of selectivity of the resulting oxidation product.

In the present invention, the layered silicate may be used in the form of a clay mineral containing a layered silicate, and examples of the clay mineral containing a layered silicate include clay minerals containing montmorillonite, such as bentonite, acid clay, and activated clay. The layered silicate may be used after calcination, and the temperature of calcination is preferably 150 to 600° C., and the calcination time is preferably 0.1 to 100 hours. Calcination may be performed in an atmosphere of an oxygen-containing gas such as air, or an atmosphere of an inert gas such as nitrogen, helium, argon, or carbon dioxide. The oxygen-containing gas and inert gas may contain steam. Calcination may be performed in a multi-stage in an atmosphere of an oxygen-containing gas or an inert gas. Calcination may be performed in a fluidized bed type or fixed bed type. The device used in calcination is not particularly limited as long as it is a device capable of heating, and it is possible to use, for example, a hot air circulation calcination furnace, a stationary type calcination furnace, a tunnel furnace, a rotary kiln, a far infrared furnace, a microwave heating furnace, and the like.

The layered silicate preferably contains cations between layers, and examples of the cation include hydrogen ion, ammonium ion, quaternary ammonium ions, cations of alkali metal elements, cations of alkali earth metal elements, cations of Group 3 metal elements, cations of Group 4 metal elements, cations of Group 5 metal elements, cations of Group 6 metal elements, cations of Group 7 metal elements, cations of Group 8 metal elements, cations of Group 9 metal elements, cations of Group 10 metal elements, cations of Group 11 metal elements, cations of Group 12 metal elements, cations of Group 13 metal elements, tin ion, lead ion, germanium ion, silicon ion, oxides of positively charged Group 4 metal elements, oxides of positively charged Group 5 metal elements, oxides of positively charged Group 6 metal elements, oxides of positively charged Group 7 metal elements, oxides of positively charged Group 8 metal elements, oxides of positively charged Group 9 metal elements, oxides of positively charged Group 10 metal elements, oxides of positively charged Group 11 metal elements, oxides of positively charged Group 12 metal elements, oxides of positively charged Group 13 metal elements, oxides of positively charged tin, oxides of positively charged lead, positively charged germanium oxides, oxides of positively charged silicon, and the like.

Of these cations in the layered silicate having cations between layers, at least one selected from the group consisting of hydrogen ion, ammonium ion, quaternary ammonium ions, cations of Group 4 metal elements, cations of Group 5 metal elements, cations of Group 6 metal elements, germanium ions, positively charged oxides of Group 4 metal elements, positively charged oxides of Group 5 metal elements, positively charged oxides of Group 6 metal elements, and positively charged germanium oxides are preferable; at least one selected from the group consisting of cations of Group 4 metal elements, germanium ions, positively charged oxides of Group 4 metal elements, and positively charged germanium oxides are more preferable; at least one selected from the group consisting of cations of Group 4 metal elements and positively charged oxides of Group 4 metal elements are still more preferable. Examples of Group 4 metal element include titanium and zirconium. Of these metal elements, titanium is preferable. Examples of the Group 5 metal element include vanadium, niobium, and tantalum. Examples of the Group 6 metal element include chromium, molybdenum, and tungsten.

When the layered silicate contains at least one selected from the group consisting of hydrogen ion, ammonium ion, quaternary ammonium ions, cations of Group 4 metal elements, cations of Group 5 metal elements, cations of Group 6 metal elements, germanium ion, oxides of positively charged Group 4 metal elements, oxides of positively charged Group 5 metal elements, oxides of positively charged Group 6 metal elements, and positively charged germanium oxides, it may further contain at least one selected from the group consisting of Group 8 metal elements, Group 9 metal elements, Group 10 metal elements, Group 11 metal elements, Group 12 metal elements, Group 13 metal elements, compounds of Group 8 metal elements, compounds of Group 9 metal elements, compounds of Group 10 metal elements, compounds of Group 11 metal elements, compounds of Group 12 metal elements, compounds of Group 13 metal elements, and oxides of positively charged silicon. Group 8 metal elements, Group 9 metal elements, Group 10 metal elements, Group 11 metal elements, Group 12 metal elements or Group 13 metal elements may be contained as cations between layers, or may be supported as a metal simple substance on the layered silicate. Compounds of Group 8 metal elements, compounds of Group 9 metal elements, compounds of Group 10 metal elements, compounds of Group 11 metal elements, compounds of Group 12 metal elements, or compounds of Group 13 metal elements compound may be contained as oxides of positively charged metal element between layers, or may be supported as metal compounds on the layered silicate. Examples of the Group 8 metal element include ruthenium, and the like. Examples of the Group 9 metal include iridium, and the like. Examples of the Group 10 metal element include nickel, palladium, platinum, and the like. Examples of the Group 11 metal elements include silver, gold, and the like. Examples of the Group 12 metal element include zinc, and the like. Examples of the Group 13 metal elements include aluminum, and the like.

Smectite to be used suitably as the layered silicate is a layered compound in which a tetrahedron sheet composed of cation and oxygen, and an octahedron sheet composed of cations and oxygen or hydroxide form a negatively charged monolayer, and cations exist between a monolayer and a monolayer. Generally, it is a layered silicate represented by the following formula (A):

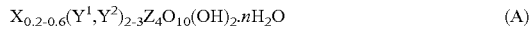

$$X_{0.2-0.6}(Y^1,Y^2)_{2-3}Z_4O_{10}(OH)_2 \cdot nH_2O \quad (A)$$

wherein X represents at least one selected from the group consisting of $K^+$, $Na^+$, $\frac{1}{2}Ca^{2+}$, and $\frac{1}{2}Mg^{2+}$, $Y^1$ represents at least one selected from the group consisting of $Mg^{2+}$, $Fe^{2+}$, $Mn^{2+}$, $Ni^{2+}$, and $Zn^{2+}$, $Y^2$ represents at least one selected from the group consisting of $Li^+$, $Al^{3+}$, $Fe^{3+}$, $Mn^{3+}$, and $Cr^{3+}$, Z represents at least one selected from the group consisting of Si and Al (excluding the case where Z is Al alone), and n≥0. X represents an interlayer cation, $Y^1$ and $Y^2$ represent cations of an octahedron sheet, and Z represents cations of a tetrahedron sheet.

In the present invention, of smectites, montmorillonite, saponite, stevensite, and hectorite are preferably used in view of selectivity of the obtained oxidation product.

Montmorillonite to be used suitably in the present invention is a layered silicate having a 2:1 type structure of silicic acid sheet/aluminic acid sheet/silicic acid sheet as a basic structure of a layer in which the layer is negatively charged by partially substituting aluminum of an aluminic acid sheet with magnesium, and exchangeable cations exist between a layer and a layer, and is generally a layered silicate represented by the following formula (B):

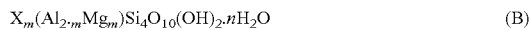

$$X_m(Al_{2-m}Mg_m)Si_4O_{10}(OH)_2 \cdot nH_2O \quad (B)$$

wherein X represents at least one selected from the group consisting of $K^+$, $Na^+$, $\frac{1}{2}Ca^{2+}$, and $\frac{1}{2}Mg^{2+}$, 0.2≤m≤0.6, and n≥0. X represents an interlayer cation.

Since the interlayer cation X in smectite or montmorillonite is exchangeable with another cation, the interlayer cation X is changeable with another cation by an ion exchange treatment of smectite or montmorillonite. It is preferred to use, as smectite or montmorillonite to be subjected to an ion exchange treatment, those having, as the interlayer cation, at least one selected from the group consisting of sodium ions, potassium ion, and calcium ion. The content of each of sodium ions, potassium ion, and calcium ion in smectite or montmorillonite can be determined by inductively coupled plasma (ICP) emission spectrometry.

It is possible to suitably used, as the layered silicate containing at least one selected from the group consisting of hydrogen ion, ammonium ion, quaternary ammonium ions, cations of Group 4 metal elements, cations of Group 5 metal elements, cations of Group 6 metal elements, germanium ions, positively charged oxides of Group 4 metal elements, positively charged oxides of Group 5 metal elements, positively charged oxides of Group 6 metal elements, and positively charged germanium oxides between layers, which is suitably used in the present invention, those obtained by subjecting a layered silicate having exchangeable cations between layers to an ion exchange treatment.

Examples of the method for preparing a layered silicate containing hydrogen ions as interlayer cations include a method in which a layered silicate having exchangeable cations between layers is subjected to an acid treatment. Examples of an acid used in the acid treatment include inorganic acids such as hydrogen chloride, nitric acid, phosphoric acid, sulfuric acid, and nitrous acid; and organic acids such as acetic acid and trifluoromethanesulfonic acid. Of these acids, the inorganic acid is preferable. Of inorganic acids, hydrogen chloride, nitric acid, and phosphoric acid are preferable. The acid treatment is preferably performed by bringing a layered silicate having exchangeable cations between layers into contact with a solution containing an acid. Interlayer cations are ion-exchanged by the acid treatment, thus enabling the preparation of a layered silicate containing hydrogen ions as the interlayer cation.

The layered silicate containing ammonium ions as the interlayer cation can be prepared, for example, by subjecting a layered silicate having exchangeable cations between layers to ion exchange treatment with at least one selected from the group consisting of ammonia and an ammonium salt. Examples of the ammonium salt include ammonium chloride, ammonium nitrate, ammonium phosphate, ammonium sulfate, and ammonium acetate and, if necessary, two or more ammonium salts thereof can also be used. The ion exchange treatment is preferably performed by bringing a layered silicate having exchangeable cations between layers into contact with at least one selected from the group consisting of ammonia and an ammonium salt. Interlayer cations X are ion-exchanged by ion exchange treatment, thus enabling the preparation of a layered silicate containing ammonium ions as the interlayer cation.

The layered silicate containing quaternary ammonium ion as the interlayer cation can be prepared, for example, by subjecting a layered silicate having exchangeable cations between layers to an ion exchange treatment with a quaternary ammonium compound. Examples of the quaternary ammonium compound include hydroxides and halides of various quaternary ammoniums such as tetramethylammonium, tetraethylammonium, n-propyltrimethylammonium, tetra-n-propylammonium, tetra-n-butylammonium, triethylmethylammonium, tri-n-propylmethylammonium, tri-n-butylmethylammonium, benzyltrimethylammonium, and dibenzyldimethylammonium and, if necessary, two or more quaternary ammonium compounds thereof can also be used. The ion exchange treatment is preferably performed by bringing a layered silicate having cations between layers into contact with a solution containing a quaternary ammonium compound. Interlayer cations are ion-exchanged by the ion exchange treatment, thus enabling the preparation of a layered silicate containing quaternary ammonium ions as the interlayer cation.

Examples of the solvent to be used in the preparation of the above-mentioned solution containing an acid, solution containing at least one selected from the group consisting of ammonia and an ammonium salt, and solution containing a quaternary ammonium compound include polar solvents such as water, methanol, ethanol, acetone, and 1,2-dimethoxyethane and, if necessary, two or more solvents thereof can also be used. Of these solvents, water is preferable. The amount of the solvent used is appropriately set. When the acid treatment is performed, the solution containing an acid preferably has a pH of 3 or lower.

The acid treatment, the ion exchange treatment with at least one selected from the group consisting of ammonia and an ammonium salt, and the ion exchange treatment with a quaternary ammonium compound may be performed in either a batch or a continuous manner. Examples of the method to be performed in a batch manner include a method in which a layered silicate having exchangeable cations between layers is immersed in the above-mentioned solution containing an acid, solution containing at least one selected from the group consisting of ammonia and an ammonium salt, or the solution containing a quaternary ammonium compound in a stirring tank, followed by mixing with stirring. Examples of the method to be performed in a continuous manner include a method in which the above-mentioned solution containing an acid, the solution containing at least one selected from the group consisting of ammonia and an ammonium salt, or solution containing a quaternary ammonium compound is made to flow through a tubular container filled with a layered silicate having exchangeable cations between layers; and a method in which a solution phase of a mixture is withdrawn while feeding the above-mentioned solution containing an acid, the solution containing at least one selected from the group consisting of ammonia and an ammonium salt, or the solution containing a quaternary ammonium compound into a stirring tank charged with a layered silicate having exchangeable cations between layers.

The temperature in the above-mentioned acid treatment, or the ion exchange treatment with at least one selected from the group consisting of ammonia and an ammonium salt, or the ion exchange treatment with a quaternary ammonium compound is usually 0 to 150° C., and preferably 20 to 100° C. The time in these treatments is usually 0.1 to 240 hours, and preferably 0.5 to 120 hours. The pressure in these treatments is usually an absolute pressure of 0.1 to 1 MPa, and preferably atmospheric pressure. The use amount of the above-mentioned solution containing an acid, the solution containing at least one selected from the group consisting of ammonia and an ammonium salt, or the solution containing a quaternary ammonium compound is appropriately set based on the layered silicate having exchangeable cations between layers. The above-mentioned acid treatment, or the ion exchange treatment with at least one selected from the group consisting of ammonia and an ammonium salt, or the ion exchange treatment with a quaternary ammonium compound may be performed a plurality of times, and these treatment may also be used in combination.

The layered silicate containing, as the interlayer cation, at least one cation selected from the group consisting of cations of Group 4 metal elements, cations of Group 5 metal elements, cations of Group 6 metal elements, and germanium ion can be prepared, for example, by subjecting a layered silicate having exchangeable cations between layers to an ion exchange treatment with at least one compound selected from the group consisting of compounds of Group 4 metal elements, compounds of Group 5 metal elements, compounds of Group 6 metal elements, and germanium compounds [hereinafter, the ion exchange treatment is sometimes referred to as an ion exchange treatment with a metal element compound]. The ion exchange treatment is preferably performed by bringing a layered silicate having exchangeable cations between layers into contact with a solution containing at least one compound selected from the group consisting of compounds of Group 4 metal elements, compounds of Group 5 metal elements, compounds of Group 6 metal elements, and germanium compounds. Interlayer cations are ion-exchanged by the ion exchange treatment, thus enabling the preparation of a layered silicate containing, as the interlayer cation, at least one cation selected from the group consisting of cations of Group 4 metal elements, cations of Group 5 metal elements, cations of Group 6 metal elements, and germanium ions. The content of at least one cation selected from the group consisting of cations of Group 4 metal elements, cations of Group 5 metal elements, cations of Group 6 metal elements, and germanium ions in the layered silicate is preferably 0.01 to 50% by weight, more preferably 0.1 to 25% by weight, and still more preferably 0.2 to 10% by weight. When two or more cations selected from the group consisting of cations of Group 4 metal elements, cations of Group 5 metal elements, cations of Group 6 metal elements, and germanium ions is contained in the layered silicate, the total content thereof may be within the above range. The content of each of cations of Group 4 metal elements, cations of Group 5 metal elements, cations of Group 6 metal elements, and germanium ions can be determined, for example, by inductively coupled plasma (ICP) emission spectrometry.

Examples of the compound of Group 4 metal elements include inorganic compounds of Group 4 metal elements and organic compounds of Group 4 metal elements. Examples of the inorganic compound of Group 4 metal elements include halides of Group 4 metal elements, such as titanium trichloride ($TiCl_3$), titanium tetrachloride ($TiCl_4$), titanium tetrabromide ($TiBr_4$), titanium tetrafluoride ($TiF_4$), titanium tetraiodide ($TiI_4$), zirconium trichloride ($ZrCl_3$), zirconium tetrachloride ($ZrCl_4$), zirconium tribromide ($ZrBr_3$), zirconium tetrabromide ($ZrBr_4$), zirconium tetrafluoride ($ZrF_4$), and zirconium tetraiodide ($ZrI_4$); nitrates of Group 4 metal elements, such as titanium tetranitrate ($Ti(NO_3)_4$) and zirconium tetranitrate ($Zr(NO_3)_4$); oxynitates of Group 4 metal elements, such as zirconyl nitrate ($ZrO(NO_3)_2$); sulfates of Group 4 metal elements, such as titanium disulfate ($Ti(SO_4)_2$) and zirconium disulfate ($Zr(SO_4)_2$); and phosphates of Group 4 metal elements, such as titanium phosphate ($Ti_3(PO_4)_4$) and zirconium phosphate ($Zr_3(PO_4)_4$). Examples of the organic compound of Group 4 metal elements include alkoxide compounds of Group 4 metal elements, such as $Ti(OR^3)_4$ (hereinafter, $R^3$ represents an alkyl group having 1 to 4 carbon atoms) and $Zr(OR^3)_4$; halogenated alkoxide compounds of Group 4 metal elements, such as $TiCl(OR^3)_3$, $TiCl_2(OR^3)_2$, $TiCl_3(OR^3)$, $ZrCl(OR^3)_3$, $ZrCl_2(OR^3)_2$, and $ZrCl_3(OR^3)$; and acetates of Group 4 metal elements, such as titanium tetraacetate ($Ti(CH_3COO)_4$) and zirconium tetraacetate ($Zr(CH_3COO)_4$). If necessary, hydrates of compounds of Group 4 metal elements may also be used, and two or more hydrates thereof may also be used. Compounds of Group 4 metal elements are preferably halides of Group 4 metal elements, sulfates of Group 4 metal elements, alkoxide compounds of Group 4 metal elements, or oxynitrates of Group 4 metal elements, and more preferably halides of Group 4 metal elements.

Examples of the compound of Group 5 metal elements include inorganic compounds of Group 5 metal elements, and organic compounds of Group 5 metal elements. Examples of the inorganic compound of Group 5 metal elements include halides of Group 5 metal elements, such as vanadium trichloride ($VCl_3$), vanadium tetrachloride ($VCl_4$), vanadium tribromide ($VBr_3$), vanadium trifluoride ($VF_3$), vanadium tetrafluoride ($VF_4$), vanadium triiodide (VI$_3$), niobium trichloride (NbCl$_3$), niobium tetrachloride (NbCl$_5$), niobium tribromide (NbBr$_3$), niobium pentabromide (NbBr$_5$), niobium pentafluoride (NbF$_5$), niobium pentaiodide (NbI$_5$), tantalum trichloride (TaCl$_3$), tantalum pentachloride (TaCl$_5$), tantalum pentabromide (TaBr$_5$), tantalum pentafluoride (TaF$_5$), and tantalum pentaiodide (TaI$_5$). Examples of the organic compound of Group 5 metal elements include alkoxide compounds of Group 5 metal elements, such as Nb(OR$^3$)$_5$ and Ta(OR$^3$)$_5$. If necessary, hydrates of compounds of Group 5 metal elements may also be used, and two or more hydrates thereof may also be used.

Examples of the compound of Group 6 metal elements include inorganic compounds of Group 6 metal elements and organic compounds of Group 6 metal elements. Examples of the inorganic compound of Group 6 metal elements include halides of Group 6 metal elements, such as chromium dichloride (CrCl$_2$), chromium trichloride (CrCl$_3$), chromium dibromide (CrBr$_2$), chromium tribromide (CrBr$_3$), chromium difluoride (CrF$_2$), chromium trifluoride (CrF$_3$), chromium diiodide (CrI$_2$), chromium triiodide (CrI$_3$), molybdenum trichloride (MoCl$_3$), molybdenum pentachloride (MoCl$_5$), molybdenum tribromide (MoBr$_3$), molybdenum tetrafluoride (MoF$_4$), molybdenum hexafluoride (MoF$_6$), tungsten tetrachloride (WCl$_4$), tungsten hexachloride (WCl$_6$), tungsten pentabromide (WBr$_5$), and tungsten hexafluoride (WF$_6$); nitrates of Group 6 metal elements, such as chromium trinitrate (Cr(NO$_3$)$_3$); and sulfates of Group 6 metal elements, such as chromium(III) sulfate (Cr$_2$(SO$_4$)$_3$). Examples of the organic compound of Group 6 metal elements include alkoxide compounds of Group 6 metal elements, such as Mo(OR$^3$)$_5$, W(OR$^3$)$_5$, and W(OR$^3$)$_6$; and. acetates of Group 6 metal elements, such as chromium triacetate (Cr(CH$_3$COO)$_3$). If necessary, hydrates of compounds of Group 6 metal elements may also be used, and two or more hydrates thereof may also be used.

Examples of the germanium compound include inorganic compounds of germanium and organic compounds of germanium. Examples of the inorganic compound of germanium include halides of germanium, such as germanium tetrachloride (GeCl$_4$), germanium tetrabromide (GeBr$_4$), germanium tetrafluoride (GeF$_4$), and germanium tetraiodide (GeI$_4$); and sulfides of germanium, such as germanium sulfide (GeS). Examples of the organic compound of germanium include alkoxide compounds of germanium, such as Ge(OR$^3$)$_4$; and halogenated alkoxide compounds of germanium, such as GeCl(OR$^3$)$_3$, GeCl$_2$(OR$^3$)$_2$, and GeCl$_3$(OR$^3$). If necessary, hydrates of germanium may also be used, and two or more hydrates thereof may also be used. Of germanium compounds, halides of germanium and alkoxide compounds of germanium are preferable.

In the above-mentioned ion exchange treatment with a metal element compound, the use amount of at least one compound selected from the group consisting of compounds of Group 4 metal elements, compounds of Group 5 metal elements, compounds of Group 6 metal elements, and germanium compounds is preferably 0.01 to 100 parts by weight, and more preferably 0.05 to 50 parts by weight, based on 100 parts by weight of a layered silicate having exchangeable cations between layers in terms of metal elements contained in at least one compound selected from the group consisting of compounds of Group 4 metal elements, compounds of Group 5 metal elements, compounds of Group 6 metal elements, and germanium compounds. When using two or more compounds selected from the group consisting of compounds of Group 4 metal elements, compounds of Group 5 metal elements, compounds of Group 6 metal elements, and germanium compounds, the total use amount thereof may be within the above range.

When the above-mentioned ion exchange treatment with a metal element compound is performed by bringing a layered silicate having exchangeable cations between layers into contact with a solution containing at least one compound selected from the group consisting of compounds of Group 4 metal elements, compounds of Group 5 metal elements, compounds of Group 6 metal elements, and germanium compounds, examples of the solvent used in the preparation of the solution include polar solvents such as water, methanol, ethanol, acetone, and 1,2-dimethoxyethane and, if necessary, two or more solvents thereof can also be used. The solution may be acidic, basic, or neutral, and it is preferred to use an aqueous acidic solution containing at least one compound selected from the group consisting of compounds of group 4 metal elements, compounds of group 5 metal elements, compounds of group 6 metal elements, and germanium compounds. If an aqueous solution prepared by mixing at least one compound selected from the group consisting of compounds of Group 4 metal elements, compounds of Group 5 metal elements, compounds of Group 6 metal elements, and germanium compounds with water has an acidic pH, the solution thus obtained may be used as it is as the aqueous acidic solution, or may be used after mixing with an acid. If an aqueous solution prepared by mixing at least one compound selected from the group consisting of compounds of Group 4 metal elements, compounds of Group 5 metal elements, compounds of Group 6 metal elements, and germanium compounds with water has not an acidic pH, an aqueous acidic solution obtained by mixing with an acid may be used.

Examples of the acid to be optionally used for the preparation of the aqueous acidic solution include an organic acid and an inorganic acid. Of these acids, an inorganic acid is preferable. Examples of the inorganic acid include hydrogen chloride, sulfuric acid, phosphoric acid, and nitric acid. The pH of the aqueous acidic solution is preferably 4 or lower. The aqueous acidic solution may also contain a polar organic solvent such as methanol, ethanol, acetone, or 1,2-dimethoxyethane. When using, as at least one compound selected from the group consisting of compounds of Group 4 metal elements, compounds of Group 5 metal elements, compounds of Group 6 metal elements, and germanium compounds, compounds to be hydrolyzed under acidic condition, such as a hydrolyzable halide, an alkoxide compound, and oxynitrate in the preparation of the aqueous acidic solution, the compound is hydrolyzed to form an oxide, thus enabling the preparation of a layered silicate in which interlayer cations are ion-exchanged with at least one selected from the group consisting of positively charged oxides of Group 4 metal elements, positively charged oxides of Group 5 metal elements, positively charged oxides of Group 6 metal elements, and positively charged germanium oxides. When using, as compounds of Group 4 metal elements, compounds of Group 5 metal elements, and compounds of Group 6 metal elements, two or more compounds of Group 4 metal elements, two or more compounds of Group 5 metal elements, or two or more compounds of Group 6 metal elements, which are hydrolyzed under acidic condition, such as hydrolysable halides, alkoxide compounds, or oxynitrate, where Group 4 metal elements, Group 5 metal elements, or Group 6 metal elements contained in these two or more compounds are not the same among the compounds, it is also possible to form a complex oxide containing, as constituent elements, two or more Group 4 metal elements, two or more Group 5 metal elements, or two or more Group 6 metal elements, thus enabling the introduction of a positively charged complex oxide containing, as interlayer cations, constituent elements such as two or more Group 4 metal elements, two or more Group 5 metal elements, or two or more Group 6 metal elements. When using two or more compounds selected from the group consisting of compounds of Group 4 metal elements, compounds of Group 5 metal elements, compounds of Group 6 metal elements, and germanium compounds, it is possible to introduce a positively charged complex oxide containing, as interlayer cations, constituent elements such as two or more metal elements selected from the group consisting of Group 4 metal elements, Group 5 metal elements, Group 6 metal elements, and germanium.

A solution containing at least one compound selected from the group consisting of compounds of Group 4 metal elements, compounds of Group 5 metal elements, compounds of Group 6 metal elements, and germanium compounds may also contain compounds of different elements, in addition to compounds of Group 4 metal elements, compounds of Group 5 metal elements, compounds of Group 6 metal elements, and germanium compound. Before and/or after bringing into contact with the solution, contact with a solution containing compounds of different elements may be performed. Examples of the compounds of the other elements include compounds of alkali metal elements, compounds of alkali earth metals of group 3 metal elements, compounds of alkali earth metals of group 7 metal elements, compounds of group 8 metal elements, compounds of group 9 metal elements, compounds of group 10 metal elements, compounds of group 11 metal elements, compounds of group 12 metal elements, compounds of group 13 metal elements, tin compounds, lead compounds, silicon compounds, arsenic compounds, antimony compounds, bismuth compounds, selenium compounds, tellurium compounds, and the like and, if necessary, two or more compounds thereof can also be used. When a silicon alkoxide compound is used as the compound of different element and a solution containing the silicon alkoxide compound is made to be acidic, oxides of positively charged silicon can be introduced into the layered silicate.

The above-mentioned ion exchange treatment with a metal element compound may be performed in either a batch or a continuous manner. Examples of the method performed in a batch manner method include a method in which a layered silicate having exchangeable cations between layers is immersed in a solution containing at least one compound selected from the group consisting of compounds of Group 4 metal elements, compounds of Group 5 metal elements, compounds of Group 6 metal elements, and germanium compounds in a stirring tank, followed by mixing with stirring. Examples of the method performed in a batch manner method include a method in which a solution containing at least one compound selected from the group consisting of compounds of Group 4 metal elements, compounds of Group 5 metal elements, compounds of Group 6 metal elements, and germanium compounds is allowed to flow through a tubular container filled with a layered silicate having exchangeable cations between layers; and a method in which a liquid phase of a mixture is withdrawn while feeding a solution containing at least one compound selected from the group consisting of compounds of Group 4 metal elements, compounds of Group 5 metal elements, compounds of Group 6 metal elements, and germanium compounds into a stirring tank charged with a layered silicate having exchangeable cations between layers.

The temperature of the above-mentioned ion exchange treatment with a metal element compound is usually 0 to 150° C., preferably 10 to 100° C., and more preferably 30 to 70° C. The time of the ion exchange treatment is usually 0.1 to 240 hours, and preferably 0.5 to 120 hours. The pressure at the time of the ion exchange treatment is usually an absolute pressure of 0.1 to 1 MPa, and preferably atmospheric pressure. The use amount of a solution containing at least one compound selected from the group consisting of compounds of Group 4 metal elements, compounds of Group 5 metal elements, compounds of Group 6 metal elements, and germanium compounds is appropriately set based on the layered silicate having exchangeable cations between layers. The above-mentioned ion exchange treatment with a metal element compound may be performed a plurality of times, if necessary. It is also possible to use in combination with at least one treatment selected from the group consisting of the above-mentioned acid treatment, the above-mentioned ion exchange treatment with at least one selected from the group consisting of ammonia and an ammonium salt, and the above-mentioned ion exchange treatment with a quaternary ammonium compound. It is possible to prepare a layered silicate containing at least one selected from the group consisting of hydrogen ions, ammonium ions, quaternary ammonium ions, cations of Group 4 metal elements, cations of Group 5 metal elements, cations of Group 6 metal elements, germanium ions, positively charged oxides of Group 4 metal elements, positively charged oxides of Group 5 metal elements, positively charged oxides of Group 6 metal elements, and positively charged germanium oxides by performing at least one treatment selected from the group consisting of the above-mentioned ion exchange treatment with a metal element compound, the above-mentioned acid treatment, the above-mentioned ion exchange treatment with at least one selected from the group consisting of ammonia and an ammonium salt, and the above-mentioned ion exchange treatment with a quaternary ammonium compound.

It is also possible to subject a layered silicate containing, as the interlayer cation, at least one cation selected from the group consisting of cations of Group 4 metal elements, cations of Group 5 metal elements, cations of Group 6 metal elements, and germanium ion to a contact treatment with the above-mentioned solution containing compounds of the other element. Such contact treatment enables supporting of at least one selected from the group consisting of the other element and compounds of the other element, or the introduction of at least one selected from the group consisting of cations of the other element and positively charged oxides of other element between layers.

The layered silicate obtained after performing at least one treatment selected from the group consisting of the above-mentioned ion exchange treatment with a metal element compound, the above-mentioned acid treatment, the above-mentioned ion exchange treatment with at least one selected from the group consisting of ammonia and an ammonium salt, and the above-mentioned ion exchange treatment with a quaternary ammonium compound is subjected to a treatment such as washing or drying, if necessary. If the layered silicate obtained after the treatment is in a slurry state, the layered silicate may be recovered by drying the slurry, or the layered silicate may be recovered by separation with filtration, decantation, or the like, followed by washing and further drying, if necessary. It is preferred that the layered silicate obtained after the treatment is subjected to washing since a layered silicate exhibiting high catalytic activity is obtained. Drying can be performed under either a normal pressure or reduced pressure, and the drying temperature is preferably 20 to 250° C., and the drying time is preferably 0.5 to 100 hours. Drying may be performed in an atmosphere of an oxygen-containing gas such as air, or an atmosphere of an inert gas such as nitrogen, helium, argon, or carbon dioxide.

After drying, calcination may be performed, if necessary. The calcination temperature is preferably 150 to 600° C., and the calcination time is preferably 0.1 to 100 hours. Calcination may be performed in an atmosphere of an oxygen-containing gas such as air, or an atmosphere of an inert gas such as nitrogen, helium, argon, or carbon dioxide. The oxygen-containing gas and inert gas may contain steam. Calcination may be performed in a multi-stage in an atmosphere of an oxygen-containing gas or an inert gas. Calcination may be performed in a fluidized bed type or fixed bed type. The device to be used in calcination is not particularly limited as long as it is a device capable of heating, and it is possible to use, for example, a hot air circulation calcination furnace, a stationary type calcination furnace, a tunnel furnace, a rotary kiln, a far infrared furnace, a microwave heating furnace, and the like.

The layered silicate may be used after molding, using a binder, or by supporting on a carrier, if necessary. Such molding treatment or supporting treatment may be performed before or after the ion exchange treatment. The molding treatment can be performed, for example, by a method such as extrusion, compression, tableting, fluidization, rolling, or spraying, and it is possible to mold the layered silicate into a desired shape, for example, granule, pellet, sphere, cylinder, plate, ring, or clover.

By using the catalyst of the present invention, and bringing the organic substrate into contact with oxygen in the presence of the catalyst, an oxidation product can be effectively produced. When an amine is used as the organic substrate, an oxime, a nitrile or a nitro compound is obtained as the oxidation product; when a hydrocarbon is used, an alcohol, an aldehyde, a ketone, a carboxylic acid, or an epoxy compound is obtained as the oxidation product; when an aldehyde is used, a carboxylic acid or an peroxide is obtained as the oxidation product; when an alcohol is used, an aldehyde, a ketone, a carboxylic acid or a peroxide is obtained as the oxidation product; and when a ketone is used, a carboxylic acid ester is obtained as the oxidation product. Of the organic substrates, when an amine is used, the method of the present invention is advantageously adopted. As the amine, the amine compound (I) is preferable, and the oxime compound (II) is effectively obtained when the amine compound (I) is used.

In the method for producing an oxidation product of the present invention, it is preferred to use an oxygen-containing gas as an oxygen source for the oxygen to be used in bringing the organic substrate into contact with oxygen. This oxygen-containing gas may be, for example, air, pure oxygen, or a gas obtained by diluting air or pure oxygen with an inert gas such as nitrogen, argon, or helium. Oxygen enriched air prepared by adding pure oxygen to air can also be used. When the oxygen-containing gas is used, the oxygen concentration in the oxygen-containing gas is preferably 1 to 30% by volume.

In the method for producing an oxidation product of the present invention, the use amount of the inorganic peroxo acid or the salt of the inorganic peroxo acid is preferably 0.01 to 1 mol, and more preferably 0.02 to 0.7 mol, based on 1 mol of the organic substrate. When the inorganic peroxo acid and the salt of the inorganic peroxo acid are used together, the total use amount should be in the range described above.

In the method for producing an oxidation product of the present invention, the use amount of the N-halogenated succinimide is preferably 0.001 to 2 mol, and more preferably 0.002 to 1 mol, based on 1 mol of the organic substrate.

In the method for producing an oxidation product of the present invention, the use amount of the nitroxide is preferably 0.001 to 1.5 mol, and more preferably 0.002 to 1 mol, based on 1 mol of the organic substrate.

In the method for producing an oxidation product of the present invention, the use amount of the peroxide is preferably 0.001 to 1.5 mol, and more preferably 0.002 to 1 mol, based on 1 mol of the organic substrate.

In the method for producing an oxidation product of the present invention, the use amount of the layered silicate is preferably 0.1 to 300 parts by weight, and more preferably 0.5 to 100 parts by weight, based on 100 parts by weight of the organic substrate.

In the method for producing an oxidation product of the present invention, the organic substrate may be brought into contact with oxygen in the presence of a solvent. Examples of the solvent include an organic solvent, water, and a mixed solvent of an organic solvent and water and, of the solvents, the organic solvent or the mixed solvent of an organic solvent and water is preferable. When the mixed solvent of an organic solvent and water is used, as the use ratio of the organic solvent and water, the weight ratio of organic solvent/water is preferably 1000 or less, and more preferably 600 or less. Examples of the organic solvent include alcohols such as methanol, ethanol, propanol, isopropanol, n-butanol, t-butanol, n-hexanol, 2-ethylhexanol, and n-dodecanol; aliphatic hydrocarbons such as pentane, hexane, heptane, octane, petroleum ether, and ligroin; alicyclic hydrocarbons such as cyclopentane, cyclohexane, and methylcyclohexane; aromatic hydrocarbon such as benzene, toluene, o-xylene, m-xylene, and p-xylene; halogenated hydrocarbons such as dichloromethane, chloroform, 1,2-dichloroethane, 1,1,1-trichloroethane, 1,1,2-trichloroethylene, 1,1,2,2-tetrachloroethylene, chlorobenzene, and o-dichlorobenzene; nitriles such as acetonitrile and benzonitrile; nitro compounds such as nitrobenzene; ester compounds such as ethyl acetate, isopropyl acetate, butyl acetate, and ethyl benzoate; and the like, and it is also possible to use two or more solvents thereof, if necessary. Of these solvents, alcohol, aromatic hydrocarbon, and nitrile are preferable. Of these alcohols, methanol, ethanol, and t-butanol are preferable. Of these aromatic hydrocarbons, toluene, o-xylene, m-xylene, and p-xylene are preferable. Of these nitriles, acetonitrile is preferable.

When using the solvent, the amount thereof is preferably 1000 parts by weight or less, and more preferably 200 parts by weight or less, based on 100 parts by weight of the organic substrate.

Contact between the organic substrate and oxygen may be performed in a batchwise manner, a semi-batchwise manner, a continuous manner, or a combination of a batchwise manner, a semi-batchwise manner, and a continuous manner. When oxidation is performed in a continuous manner, oxidation can be carried out by various manners such as extraction of a liquid phase of the reaction mixture while feeding a reaction starting material into a fixed bed type, fluidized bed type, moving bed type, suspension type, stirring/mixing type, or loop type reactor.

The temperature in the contact between the organic substrate and oxygen is preferably 50 to 200° C., and more preferably 70 to 150° C. The reaction pressure is usually an absolute pressure of 0.1 to 10 MPa, and preferably 0.2 to 7.0 MPa. The contact between the organic substrate and oxygen is preferably performed under pressure, and in this case, the pressure may be adjusted using an inert gas such as nitrogen or helium. When the contact between the organic substrate and oxygen is performed in a stirring/mixing type reactor under liquid phase in a batchwise or continuous manner using an oxygen-containing gas, an oxygen-containing gas may be fed to a vapor phase portion of a reactor, or an oxygen-containing gas may be fed in a liquid phase, or an oxygen-containing gas may be fed in a vapor phase portion and a liquid phase of a reactor.

In the contact between the organic substrate and oxygen, a radical initiator, a phenol-based chain transfer agent, and the like may be allowed to coexist appropriately, in addition to the inorganic peroxo acid, the salt of the inorganic peroxo acid, the N-halogenated succinimide, the nitroxide and the peroxide. Examples of the radical initiator include a hydrazyl radical and a hydrazine compound disclosed in WO 2005/009613 A; and an azo compound disclosed in JP 2005-15381 A and, if necessary, two or more radical initiators may be used. Examples of the hydrazyl radical include 2,2-diphenyl-1-picrylhydrazyl, 2,2-di(4-tert-octylphenyl)-1-picrylhydrazyl. Examples of the hydrazine compound include 1,1-diphenyl-2-picrylhydrazine. Examples of the phenol-based chain transfer agent include compounds disclosed in JP 2005-15382 A. The use amount of the radical initiator or the phenol-based chain transfer agent is appropriately set, considering production cost and productivity.

Post treatment operations of the reaction mixture containing the oxidation product obtained by the contact between the organic substrate and oxygen can be appropriately selected, and the oxidation product can be used for various applications after purifying using treatments such as filtration, washing, distillation, crystallization, extraction, recrystallization, and chromatography in combination, if necessary. A catalyst recovered after the contact between the organic substrate and oxygen can be reused after subjecting to treatments such as washing, calcination, and ion exchange treatment, if necessary. When the reaction mixture contains a solvent and an unreacted material, the solvent and unreacted material recovered can be reused.

When the amine compound (I) is used as the organic substrate, the obtained oxime compound (II) is suitably used as a starting material for the production of the amide compound (III) after allowing to undergo a Beckmann rearrangement reaction.

When, in the amide compound (III), $R^1$ and $R^2$ are taken together with the nitrogen atom to which $R^1$ is attached and the carbon atom to which $R^2$ is attached to form an optionally substituted alicyclic hydrocarbon group having 3 to 12 carbon atoms, the amide compound (III) means a corresponding amide compound (III) which is obtained by allowing an oxime compound (II) to undergo a Beckmann rearrangement reaction, in the case where, in the oxime compound (II), $R^1$ and $R^2$ are taken together with the carbon atom to which $R^1$ and $R^2$ are attached to form an optionally substituted alicyclic hydrocarbon group having 3 to 12 carbon atoms.

Examples of such a Beckmann rearrangement reaction include a method which is performed under a liquid phase condition, and a method which is performed under a vapor phase condition. Examples of the Beckmann rearrangement reaction under a liquid phase condition include a method which is performed in the presence of a strong acid such as fuming sulfuric acid, and can be performed in accordance with the method mentioned in JP 48-4791 A. Examples of the Beckmann rearrangement reaction under a vapor phase condition include a method which is performed in the presence of a solid catalyst such as zeolite, and can be performed in accordance with the method mentioned in JP 5-170732 A. For example, when using cyclohexylamine as the amine compound (I), ε-caprolactam can be produced by the Beckmann rearrangement reaction of cyclohexanone oxime obtained by the contact with oxygen.

EXAMPLES

The present invention will be described by way of the following Examples and Comparative Examples, but it is not construed to limit the present invention thereto. In the following Examples, cyclohexylamine [compound of the formula (I) in which $R^1$ and $R^2$ are taken together with the carbon atom to which $R^1$ and $R^2$ are attached to form a cyclohexane ring] and cyclohexanone oxime [compound of the formula (II) in which $R^1$ and $R^2$ are taken together with the carbon atom to which $R^1$ and $R^2$ are attached to form a cyclohexane ring] in the reaction solution were analyzed by gas chromatography, and the conversion ratio of cyclohexylamine, the selectivity to cyclohexanone oxime and the yield of cyclohexanone oxime were calculated.

Reference Example 1

Preparation of Catalyst A

In a 2 L poly beaker, 558 g of 1,2-dimethoxyethane (manufactured by Wako Pure Chemical Industries, Ltd.) and 141.59 g of 30% by weight nitric acid (manufactured by Wako Pure Chemical Industries, Ltd.) were charged, 18.01 g of a 20% by weight titanium trichloride solution (dilute hydrochloric acid solution of $TiCl_3$, manufactured by Wako Pure Chemical Industries, Ltd.) was added while stirring the obtained mixed solution, followed by stirring at room temperature for 5 minutes. To the obtained mixed solution, 15 g of montmorillonite (Kunipia F, manufactured by KUNIMINE INDUSTRIES CO., LTD., montmorillonite containing sodium ions, potassium ions, and calcium ions as interlayer cations) was added, the mixture was stirred at room temperature for 5 minutes, and a vapor phase portion in the poly beaker was replaced by nitrogen. Using a water bath, the temperature was raised to 50° C. while stirring the mixture in the poly beaker, and the stirring was continued at 50° C. for 6 hours. After a lapse of 6 hours, cooling to room temperature was performed and stirring was stopped. A solid was separated by pressure filtration of the obtained mixture, and this solid was washed with water and filtered by pressure filtration, and then repeatedly washed until the pH of the washing filtrate became 5 or higher. After washing, the obtained solid was dried overnight at 110° C., thereby preparing a catalyst A (montmorillonite containing titanium ions between layers).

Reference Example 2

Preparation of Catalyst B

In a 2 L poly beaker, 700 g of 1,2-dimethoxyethane (manufactured by Wako Pure Chemical Industries, Ltd.) was charged, 1.71 g of a 20% by weight titanium trichloride solution (dilute hydrochloric acid solution of $TiCl_3$, manufacture by Wako Pure Chemical Industries, Ltd.) was added while stirring, followed by stirring at room temperature for 5 minutes. To the obtained mixed solution, 15 g of montmorillonite (Kunipia F, manufactured by KUNIMINE INDUSTRIES CO., LTD., montmorillonite containing sodium ions, potassium ions, and calcium ions as interlayer cations) was added, the mixture was stirred at room temperature for 5 minutes, and a vapor phase portion in the poly beaker was replaced by nitrogen. Using a water bath, the temperature was raised to 50° C. while stirring the mixture in the poly beaker, and the stirring was continued at 50° C. for 6 hours. After a lapse of 6 hours, cooling to room temperature was performed and stirring was stopped. A solid was separated by pressure filtration of the obtained mixture, and this solid was washed with water and filtered by pressure filtration, and repeatedly washed until the pH of the washing filtrate became 5 or higher. After washing, the obtained solid was dried overnight at 110° C., thereby preparing a catalyst B (montmorillonite containing titanium ions between layers).

Reference Example 3

Preparation of Catalyst C

In a 500 mL recovery flask, 50.7 g of deionized water and 5.1 g of the catalyst A obtained in Reference Example 1 was charged, followed by stirring at room temperature for 5 minutes. To the obtained mixture, 0.12 g of ruthenium chloride hydrate (manufactured by FURUYA METAL Co., Ltd., Ru content of 40.75% by weight) was added, followed by stirring at room temperature for 5 minutes. Next, a solid was separated by distilling off water from the obtained mixture at 50° C. under reduced pressure using a rotary evaporator. This solid was calcined at 450° C. under air flow for 6 hours, thereby preparing a catalyst C.

Reference Example 4

Preparation of Catalyst D

In a 100 mL beaker, 15.9 g of methanol (manufactured by Wako Pure Chemical Industries, Ltd.) and 8.0 g of 2 mol/L hydrochloric acid (manufactured by Wako Pure Chemical Industries, Ltd.) were charged and 33.6 g of tetraethyl orthosilicate (manufactured by Wako Pure Chemical Industries, Ltd.) was added while stirring the obtained mixture. After the temperature was raised to 70° C. while stirring using a water bath, followed by continuous stirring at 70° C. for 1 hour, thereby preparing a solution a. Meanwhile, 48.0 g of 2 mol/L hydrochloric acid (manufactured by Wako Pure Chemical Industries, Ltd.) and 4.8 g of titanium tetraisopropoxide (manufactured by Wako Pure Chemical Industries, Ltd.) were charged into a 100 mL beaker, followed by stirring at room temperature for 1 hour, thereby preparing a solution b.

In a 1 L poly beaker, 250 g of methanol (manufactured by Wako Pure Chemical Industries, Ltd.) and 40.0 g of stevensite (IONITE, manufactured by Mizusawa Industrial Chemicals, Ltd.) were charged, followed by stirring at room temperature for 5 minutes. Using a water bath, the temperature was raised to 50° C. while stirring the mixture in the poly beaker, and then a mixed solution of the total amount of the solution a and the total amount of the solution b was added dropwise over 1 hour. After completion of the dropwise addition, stirring was continued at 50° C. for 6 hours. After a lapse of 6 hours, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C., thereby preparing a catalyst D.

Reference Example 5

Preparation of Catalyst E

The same operation as in Reference Example 4 was performed, except that 40.0 g of stevensite (Sumecton ST, manufactured by KUNIMINE INDUSTRIES CO., LTD.) was used in place of 40.0 g of stevensite (IONITE, manufactured by Mizusawa Industrial Chemicals, Ltd.), thereby preparing a catalyst E.

Example 1

In a reactor made of SUS316 (volume: 200 mL) equipped with a thermocouple, a magnetic stirrer, a gas feed line, and a gas discharge line, 1.47 g (14.8 mmol) of cyclohexylamine (manufactured by Wako Pure Chemical Industries, Ltd.), 2.40 g (KHSO$_5$: 7.81 mmol) of OXONE (registered trademark) (manufactured by Sigma-Aldrich, KHSO$_5$.0.5KHSO$_4$.0.5K$_2$SO$_4$), and 7.05 g of acetonitrile (manufacture by Wako Pure Chemical Industries, Ltd.) were charged and a vapor phase portion in the reactor was replaced by a nitrogen gas. After the reactor was sealed, a mixed gas of oxygen and nitrogen (oxygen concentration: 7% by volume) was introduced into the vapor phase portion in the reactor to thereby adjust the pressure in the reactor to 0.90 MPa (gauge pressure). Next, the temperature of the mixture in the reactor was raised to 80° C. while stirring. The pressure in the reactor was 1.05 MPa (gauge pressure). After keeping the reactor warm at 80° C. for 4 hours while continuing to stir, cooling was performed. The obtained reaction mixture was diluted by the addition of methanol and filtered, and then the obtained filtrate was analyzed. As a result, the conversion ratio of cyclohexylamine was 34.2% and the selectivity to cyclohexanone oxime was 66.2%.

Example 2

The same operation as in Example 1 was performed, except that 7.19 g of toluene (manufactured by Wako Pure Chemical Industries, Ltd.) was used in place of 7.05 g of acetonitrile. The obtained filtrate was analyzed. As a result, the conversion ratio of cyclohexylamine was 18.2% and the selectivity to cyclohexanone oxime was 59.6%.

Example 3

The same operation as in Example 1 was performed, except that 7.18 g of a mixed solution of t-butanol and water [t-butanol/water=7/1 (weight ratio)] was used in place of 7.05 g of acetonitrile. The obtained filtrate was analyzed. As a result, the conversion ratio of cyclohexylamine was 49.9% and the selectivity to cyclohexanone oxime was 62.3%.

Example 4

In a reactor made of SUS316 (volume: 200 mL) equipped with a thermocouple, a magnetic stirrer, a gas feed line, and a gas discharge line, 0.30 g of the catalyst A obtained in Reference Example 1, 1.47 g (14.8 mmol) of cyclohexylamine (manufacture by Wako Pure Chemical Industries, Ltd.), 0.28 g (KHSO$_5$: 0.91 mmol) of OXONE (registered trademark) (manufactured by Sigma-Aldrich, KHSO$_5$.0.5KHSO$_4$.0.5K$_2$SO$_4$), and 7.10 g of toluene (manufactured by Wako Pure Chemical Industries, Ltd.) were charged and a vapor phase portion in the reactor was replaced by a nitrogen gas. After the reactor was sealed, a mixed gas of oxygen and nitrogen (oxygen concentration: 7% by volume) was introduced into the vapor phase portion in the reactor to thereby adjust the pressure in the reactor to 0.90 MPa (gauge pressure). Next, the temperature of the mixture in the reactor was raised to 80° C. while stirring. The pressure in the reactor was 1.05 MPa (gauge pressure). After keeping the reactor warm at 80° C. for 4 hours while continuing to stir, cooling was performed. The obtained reaction mixture was diluted by the addition of methanol and filtered, and then the obtained filtrate was analyzed. As a result, the conversion ratio of cyclohexylamine was 3.0% and the selectivity to cyclohexanone oxime was 77.6%.

Example 5

The same operation as in Example 4 was performed, except that the use amount of OXONE (registered trademark) was changed from 0.28 g to 1.36 g (KHSO$_5$: 4.42 mmol). The obtained filtrate was analyzed. As a result, the conversion ratio of cyclohexylamine was 8.4% and the selectivity to cyclohexanone oxime was 78.9%.

Example 6

The same operation as in Example 4 was performed, except that the use amount of OXONE (registered trademark) was changed from 0.28 g to 2.71 g (KHSO$_5$: 8.82 mmol). The obtained filtrate was analyzed. As a result, the conversion ratio of cyclohexylamine was 13.6% and the selectivity to cyclohexanone oxime was 81.2%.

Example 7

The same operation as in Example 4 was performed, except that 7.02 g of acetonitrile (manufactured by Wako Pure Chemical Industries, Ltd.) was used in place of 7.10 g of toluene. The obtained filtrate was analyzed. As a result, the conversion ratio of cyclohexylamine was 3.8% and the selectivity to cyclohexanone oxime was 79.0%.

Example 8

The same operation as in Example 4 was performed, except that 0.30 g of the catalyst B obtained in Reference Example 2 was used in place of 0.30 g of the catalyst A, and the use amount of toluene was changed from 7.10 g to 6.97 g. The obtained filtrate was analyzed. As a result, the conversion ratio of cyclohexylamine was 3.2% and the selectivity to cyclohexanone oxime was 73.1%.

Example 9

The same operation as in Example 8 was performed, except that 7.00 g of acetonitrile (manufactured by Wako Pure Chemical Industries, Ltd.) was used in place of 6.97 g of toluene. The obtained filtrate was analyzed. As a result, the conversion ratio of cyclohexylamine was 4.2% and the selectivity to cyclohexanone oxime was 83.6%.

Example 10

The same operation as in Example 8 was performed, except that 7.13 g of a mixed solution of t-butanol and water [t-butanol/water=7/1 (weight ratio)] was used in place of 6.97 g of toluene. The obtained filtrate was analyzed. As a result, the conversion ratio of cyclohexylamine was 3.9% and the selectivity to cyclohexanone oxime was 80.7%.

Example 11

The same operation as in Example 8 was performed, except that the use amount of OXONE (registered trademark) was changed from 0.28 g to 2.40 g (KHSO$_5$: 7.81 mmol), and the use amount of toluene was changed from 6.97 g to 7.10 g. The obtained filtrate was analyzed. As a result, the conversion ratio of cyclohexylamine was 21.6% and the selectivity to cyclohexanone oxime was 69.4%.

Example 12

The same operation as in Example 11 was performed, except that 7.02 g of acetonitrile (manufactured by Wako Pure Chemical Industries, Ltd.) was used in place of 7.10 g of toluene. The obtained filtrate was analyzed. As a result, the conversion ratio of cyclohexylamine was 17.1% and the selectivity to cyclohexanone oxime was 79.0%.

Example 13

The same operation as in Example 11 was performed, except that 7.18 g of a mixed solution of t-butanol and water [t-butanol/water=7/1 (weight ratio)] was used in place of 7.10 g of toluene. The obtained filtrate was analyzed. As a result, the conversion ratio of cyclohexylamine was 41.6% and the selectivity to cyclohexanone oxime was 70.9%.

Example 14

The same operation as in Example 9 was performed, except that 0.10 g (0.42 mmol) of sodium peroxodisulfate (manufactured by Wako Pure Chemical Industries, Ltd.) was used in place of 0.28 g of OXONE (registered trademark). The obtained filtrate was analyzed. As a result, the conversion ratio of cyclohexylamine was 9.1% and the selectivity to cyclohexanone oxime was 56.8%.

Example 15

The same operation as in Example 9 was performed, except that 0.11 g (0.40 mmol) of potassium peroxodisulfate (manufactured by Wako Pure Chemical Industries, Ltd.) was used in place of 0.28 g of OXONE (registered trademark). The obtained filtrate was analyzed. As a result, the conversion ratio of cyclohexylamine was 7.7% and the selectivity to cyclohexanone oxime was 57.5%.

Example 16

The same operation as in Example 9 was performed, except that 0.09 g (0.37 mmol) of ammonium peroxodisulfate (manufactured by Wako Pure Chemical Industries, Ltd.) was used in place of 0.28 g of OXONE (registered trademark). The obtained filtrate was analyzed. As a result, the conversion ratio of cyclohexylamine was 9.4% and the selectivity to cyclohexanone oxime was 59.2%.

Example 17

The same operation as in Example 15 was performed, except that the use amount of potassium peroxodisulfate (manufactured by Wako Pure Chemical Industries, Ltd.) was changed from 0.11 g to 1.02 g (3.74 mmol). The obtained filtrate was analyzed. As a result, the conversion ratio of cyclohexylamine was 14.0% and the selectivity to cyclohexanone oxime was 55.1%.

Example 18

In a reactor made of SUS316 (volume: 100 mL) equipped with a thermocouple, a magnetic stirrer, a gas feed line, and a gas discharge line, 0.30 g of the catalyst B obtained in Reference Example 2, 1.49 g (15.0 mmol) of cyclohexylamine (manufactured by Wako Pure Chemical Industries, Ltd.), 0.014 g (0.075 mmol) of N-bromosuccinimide (manufactured by Tokyo Chemical Industry Co., Ltd.), and 2.24 g of toluene (manufactured by Wako Pure Chemical Industries, Ltd.) were charged and a vapor phase portion in the reactor was replaced by a nitrogen gas. After the reactor was sealed, a mixed gas of oxygen and nitrogen (oxygen concentration: 7% by volume) was introduced into the vapor phase portion in the reactor to thereby adjust the pressure in the reactor to 0.90 MPa (gauge pressure). Next, the temperature of the mixture in the reactor was raised to 130° C. while stirring. The pressure in the reactor was 1.05 MPa (gauge pressure). After keeping the reactor warm at 130° C. for 4 hours while continuing to stir, cooling was performed. The obtained reaction mixture was diluted by the addition of methanol and filtered, and then the obtained filtrate was analyzed. As a result, the yield of cyclohexanone oxime was 7.3%.

Example 19

The same operation as in Example 18 was performed, except that the use amount of N-bromosuccinimide was changed from 0.014 g to 0.57 g (3.08 mmol), and 2.25 g of acetonitrile (manufactured by Wako Pure Chemical Industries, Ltd.) was used in place of 2.24 g of toluene. The obtained filtrate was analyzed. As a result, the yield of cyclohexanone oxime was 7.2%.

Example 20

The same operation as in Example 18 was performed, except that temperature rise to 130° C. was replaced by temperature rise to 100° C. and the reaction was continued at 100° C. for 4 hours. The pressure in the reactor was 1.03 MPa (gauge pressure) when the temperature was raised to 100° C. The obtained filtrate was analyzed. As a result, the yield of cyclohexanone oxime was 14.8%.

Example 21

The same operation as in Example 18 was performed, except that temperature rise to 130° C. was replaced by temperature rise to 95° C., and the reaction was continued at 95° C. for 3 hours. The pressure in the reactor was 1.03 MPa (gauge pressure) when the temperature was raised to 95° C. The obtained filtrate was analyzed. As a result, the yield of cyclohexanone oxime was 15.0%.

Example 22

The same operation as in Example 18 was performed, except that temperature rise to 130° C. was replaced by temperature rise to 95° C., and the reaction was continued at 95° C. for 5 hours. The pressure in the reactor was 1.03 MPa (gauge pressure) when the temperature was raised to 95° C. The obtained filtrate was analyzed. As a result, the yield of cyclohexanone oxime was 27.8%.

Example 23

The same operation as in Example 18 was performed, except that 0.012 g (0.075 mmol) of 2,2,6,6-tetramethylpiperidine-1-oxyl (manufactured by Sigma-Aldrich) was used in place of 0.014 g of N-bromosuccinimide. The obtained filtrate was analyzed. As a result, the yield of cyclohexanone oxime was 18.4%.

Example 24

The same operation as in Example 23 was performed, except that the use amount of 2,2,6,6-tetramethylpiperidine-1-oxyl was changed from 0.012 g to 0.16 g (1.08 mmol), and 2.25 g of acetonitrile (manufactured by Wako Pure Chemical Industries, Ltd.) was used in place of 2.24 g of toluene. The obtained filtrate was analyzed. As a result, the yield of cyclohexanone oxime was 18.4%.

Example 25

The same operation as in Example 18 was performed, except that 0.024 g (0.075 mmol) of benzoyl peroxide (manufactured by Kayaku Akuzo Corporation, Perkadox L-W75, purity 75.4%) was used in place of 0.014 g of N-bromosuccinimide. The obtained filtrate was analyzed. As a result, the yield of cyclohexanone oxime was 17.2%.

Example 26

The same operation as in Example 25 was performed, except that the use amount of benzoyl peroxide was changed from 0.024 g to 0.69 g (2.08 mmol), and 2.25 g of acetonitrile (manufactured by Wako Pure Chemical Industries, Ltd.) was used in place of 2.24 g of toluene. The obtained filtrate was analyzed. As a result, the yield of cyclohexanone oxime was 18.2%.

Example 27

In a reactor made of SUS316 (volume: 100 mL) equipped with a thermocouple, a magnetic stirrer, a gas feed line, and a gas discharge line, 0.30 g of the catalyst B obtained in Reference Example 2, 1.49 g (15.0 mmol) of cyclohexylamine (manufactured by Wako Pure Chemical Industries, Ltd.), 0.014 g (0.075 mmol) of N-bromosuccinimide (manufactured by Tokyo Chemical Industry Co., Ltd.), 0.012 g (0.075 mmol) of 2,2,6,6-tetramethylpiperidine-1-oxyl (manufactured by Sigma-Aldrich) and 2.25 g of acetonitrile (manufactured by Wako Pure Chemical Industries, Ltd.) were charged and a vapor phase portion in the reactor was replaced by a nitrogen gas. After the reactor was sealed, a mixed gas of oxygen and nitrogen (oxygen concentration: 7% by volume) was introduced into the vapor phase portion in the reactor to thereby adjust the pressure in the reactor to 0.90 MPa (gauge pressure). Next, the temperature of the mixture in the reactor was raised to 130° C. while stirring. The pressure in the reactor was 1.05 MPa (gauge pressure). After keeping the reactor warm at 130° C. for 4 hours while continuing to stir, cooling was performed. The obtained reaction mixture was diluted by the addition of methanol and filtered, and then the obtained filtrate was analyzed. As a result, the yield of cyclohexanone oxime was 18.6%.

Example 28

In a reactor made of SUS316 (volume: 100 mL) equipped with a thermocouple, a magnetic stirrer, a gas feed line, and a gas discharge line, 0.30 g of the catalyst B obtained in Reference Example 2, 1.49 g (15.0 mmol) of cyclohexylamine (manufactured by Wako Pure Chemical Industries, Ltd.), 0.0056 g (0.030 mmol) of N-bromosuccinimide (manufactured by Tokyo Chemical Industry Co., Ltd.), 0.0048 g (0.030 mmol) of 2,2,6,6-tetramethylpiperidine-1-oxyl (manufactured by Sigma-Aldrich), and 2.23 g of toluene (manufactured by Wako Pure Chemical Industries, Ltd.) were charged and a vapor phase portion in the reactor was replaced by a nitrogen gas. After the reactor was sealed, a mixed gas of oxygen and nitrogen (oxygen concentration: 7% by volume) was introduced into the vapor phase portion in the reactor to thereby adjust the pressure in the reactor to 0.90 MPa (gauge pressure). Next, the temperature of the mixture in the reactor was raised to 90° C. while stirring. The pressure in the reactor was 1.02 MPa (gauge pressure). After keeping the reactor warm at 90° C. for 4 hours while continuing to stir, cooling was performed. The obtained reaction mixture was diluted by the addition of methanol and filtered, and then the obtained filtrate was analyzed. As a result, the yield of cyclohexanone oxime was 18.4%.

Example 29

The same operation as in Example 27 was performed, except that 0.024 g (0.075 mmol) of benzoyl peroxide (manufactured by Kayaku Akuzo Corporation, Perkadox L-W75, purity 75.4%) was used in place of 0.014 g of N-bromosuccinimide. The obtained filtrate was analyzed. As a result, the yield of cyclohexanone oxime was 18.5%.

Example 30

In a reactor made of SUS316 (volume: 350 mL) equipped with a thermocouple, a magnetic stirrer, a gas feed line, and a gas discharge line, 9.00 g of the catalyst C obtained in Reference Example 3, 49.9 g (0.50 mol) of cyclohexylamine (manufactured by Wako Pure Chemical Industries, Ltd.), 0.30 g (1.5 mmol) of N-bromosuccinimide (manufactured by Tokyo Chemical Industry Co., Ltd.), 4.90 g (0.27 mol) of water, and 44.9 g of toluene (manufactured by Wako Pure Chemical Industries, Ltd.) were charged and a vapor phase portion in the reactor was replaced by a mixed gas of oxygen and nitrogen (oxygen concentration: 4% by volume). After the reactor was sealed, a mixed gas of oxygen and nitrogen (oxygen concentration: 4% by volume) was introduced into the vapor phase portion in the reactor to thereby adjust the pressure in the reactor to 5.00 MPa (gauge pressure). Next, the temperature was raised to 90° C. while stirring. The pressure in the reactor was 5.00 MPa (gauge pressure). Then, while continuing to stir, a mixture of cyclohexylamine/N-bromosuccinimide/water/toluene=49.9/0.3/4.9/44.9 (weight ratio) was continuously fed into the reactor at a flow rate of 20 g/hour (retention time 5 hours), and a mixed gas of oxygen and nitrogen (oxygen concentration: 4% by volume) was allowed to flow through the reactor by blowing into a liquid phase of the mixture in the reactor at a flow rate of 20 L/hour to thereby initiate the reaction. While maintaining the pressure in the reactor at 5.00 MPa (gauge pressure), the mixture in the reactor was continuously withdrawn at a flow rate of 20 g/hour through a sintered metal filter made of stainless steel (SUS316), and the reaction was continued at 90° C. for 5 hours while discharging the gas from the vapor phase portion in the reactor via a gas discharge line and then feed of the mixed gas of oxygen and nitrogen was stopped, followed by cooling. The obtained reaction mixture was diluted by the addition of methanol and filtered, and then the obtained filtrate was analyzed. As a result, the conversion ratio of cyclohexylamine was 14.1%, the selectivity to cyclohexanone oxime was 81.0%, and the yield of cyclohexanone oxime was 11.4%.

Example 31

In a reactor made of SUS316 (volume: 350 mL) equipped with a thermocouple, a magnetic stirrer, a gas feed line, and a gas discharge line, 9.00 g of the catalyst C obtained in Reference Example 3, 49.9 g (0.50 mol) of cyclohexylamine (manufactured by Wako Pure Chemical Industries, Ltd.), 0.90 g (4.5 mmol) of N-bromosuccinimide (manufactured by Tokyo Chemical Industry Co., Ltd.), 4.90 g (0.27 mol) of water, and 44.3 g of toluene (manufactured by Wako Pure Chemical Industries, Ltd.) were charged and a vapor phase portion in the reactor was replaced by a mixed gas of oxygen and nitrogen (oxygen concentration: 4% by volume). After the reactor was sealed, a mixed gas of oxygen and nitrogen (oxygen concentration: 4% volume) was introduced into the vapor phase portion in the reactor to thereby adjust the pressure in the reactor to 5.00 MPa (gauge pressure). Next, the temperature was raised to 90° C. while stirring. The pressure in the reactor was 5.00 MPa (gauge pressure). Then, while continuing to stir, a mixture of cyclohexylamine/N-bromosuccinimide/water/toluene=49.9/0.9/4.9/44.3 (weight ratio) was continuously fed into the reactor at a flow rate of 20 g/hour (retention time 5 hours), and a mixed gas of oxygen and nitrogen (oxygen concentration: 4% by volume) was allowed to flow through the reactor by blowing into a liquid phase of the mixture in the reactor at a flow rate of 20 L/hour to thereby initiate the reaction. While maintaining the pressure in the reactor at 5.00 MPa (gauge pressure), the mixture in the reactor was continuously withdrawn at a flow rate of 20 g/hour through a sintered metal filter made of stainless steel (SUS316), and the reaction was continued at 90° C. for 5 hours while discharging the gas from the vapor phase portion in the reactor via a gas discharge line and then feed of the mixed gas of oxygen and nitrogen was stopped, followed by cooling. The obtained reaction mixture was diluted by the addition of methanol and filtered, and then the obtained filtrate was analyzed. As a result, the conversion ratio of cyclohexylamine was 22.6%, the selectivity to cyclohexanone oxime was 82.6% and the yield of cyclohexanone oxime was 18.7%.

Example 32

In a reactor made of SUS316 (volume: 350 mL) equipped with a thermocouple, a magnetic stirrer, a gas feed line, and a gas discharge line, 9.00 g of the catalyst D obtained in Reference Example 4, 49.9 g (0.50 mol) of cyclohexylamine (manufactured by Wako Pure Chemical Industries, Ltd.), 1.80 g (9.0 mmol) of N-bromosuccinimide (manufactured by Tokyo Chemical Industry Co., Ltd.), 9.90 g (0.55 mol) of water, and 38.3 g of toluene (manufactured by Wako Pure Chemical Industries, Ltd.) were charged and a vapor phase portion in the reactor was replaced by a mixed gas of oxygen and nitrogen (oxygen concentration: 6% by volume). After the reactor was sealed, a mixed gas of oxygen and nitrogen (oxygen concentration: 6% by volume) was introduced into the vapor phase portion in the reactor to thereby adjust the pressure in the reactor to 5.00 MPa (gauge pressure). Next, the temperature was raised to 90° C. while stirring. The pressure in the reactor was 5.00 MPa (gauge pressure). Then, while continuing to stir, a mixture of cyclohexylamine/N-bromosuccinimide/water/toluene=49.9/1.8/9.9/38.3 (weight ratio) was continuously fed into the reactor at a flow rate of 25 g/hour (retention time 4 hours), and a mixed gas of oxygen and nitrogen (oxygen concentration: 6% by volume) was allowed to flow through the reactor by blowing into a liquid phase of the mixture in the reactor at a flow rate of 30 L/hour to thereby initiate the reaction. While maintaining the pressure in the reactor at 5.00 MPa (gauge pressure), the mixture in the reactor was continuously withdrawn at a flow rate of 25 g/hour through a sintered metal filter made of stainless steel (SUS316), and the reaction was continued at 90° C. for 4 hours while discharging the gas from the vapor phase portion in the reactor via a gas discharge line and then feed of the mixed gas of oxygen and nitrogen was stopped, followed by cooling. The obtained reaction mixture was diluted with the addition of methanol and filtered, and then the resulting filtrate was analyzed. As a result, the conversion ratio of cyclohexylamine was 26.7%, the selectivity to cyclohexanone oxime was 85.4% and the yield of cyclohexanone oxime was 22.8%.

Example 33

In a reactor made of SUS316 (volume: 350 mL) equipped with a thermocouple, a magnetic stirrer, a gas feed line, and a gas discharge line, 9.00 g of the catalyst D obtained in Reference Example 4, 49.9 g (0.50 mol) of cyclohexylamine (manufactured by Wako Pure Chemical Industries, Ltd.), 0.90 g (4.5 mmol) of N-bromosuccinimide (manufactured by Tokyo Chemical Industry Co., Ltd.), 4.90 g (0.27 mol) of water, and 44.9 g of toluene (manufactured by Wako Pure Chemical Industries, Ltd.) were charged and a vapor phase portion in the reactor was replaced by a mixed gas of oxygen and nitrogen (oxygen concentration: 4% by volume). After the reactor was sealed, a mixed gas of oxygen and nitrogen (oxygen concentration: 4% by volume) was introduced into the vapor phase portion in the reactor to thereby adjust the pressure in the reactor to 5.00 MPa (gauge pressure). Next, the temperature was raised to 90° C. while stirring. The pressure in the reactor was 5.00 MPa (gauge pressure). Then, while continuing to stir, a mixture of cyclohexylamine/N-bromosuccinimide/water/toluene=49.9/0.9/4.9/44.9 (weight ratio) was continuously fed into the reactor at a flow rate of 12.5 g/hour (retention time 8 hours), and a mixed gas of oxygen and nitrogen (oxygen concentration: 4% by volume) was allowed to flow through the reactor by blowing into a liquid phase of the mixture in the reactor at a flow rate of 20 L/hour to thereby initiate the reaction. While maintaining the pressure in the reactor at 5.00 MPa (gauge pressure), the mixture in the reactor was continuously withdrawn at a flow rate of 12.5 g/hour through a sintered metal filter made of stainless steel (SUS316), and the reaction was continued at 90° C. for 8 hours while discharging the gas from the vapor phase portion in the reactor via a gas discharge line and then feed of the mixed gas of oxygen and nitrogen was stopped, followed by cooling. The obtained reaction mixture was diluted by the addition of methanol and filtered, and then the obtained filtrate was analyzed. As a result, the conversion ratio of cyclohexylamine was 40.9%, the selectivity to cyclohexanone oxime was 85.6% and the yield of cyclohexanone oxime was 35.0%.

Example 34

In a reactor made of SUS316 (volume: 350 mL) equipped with a thermocouple, a magnetic stirrer, a gas feed line, and a gas discharge line, 9.00 g of the catalyst E obtained in Reference Example 5, 49.9 g (0.50 mol) of cyclohexylamine (manufactured by Wako Pure Chemical Industries, Ltd.), 0.90 g (4.5 mmol) of N-bromosuccinimide (manufactured by Tokyo Chemical Industry Co., Ltd.), 4.90 g (0.27 mol) of water, and 44.9 g of toluene (manufactured by Wako Pure Chemical Industries, Ltd.) were charged and a vapor phase portion in the reactor was replaced by a mixed gas of oxygen and nitrogen (oxygen concentration: 4% by volume). After the reactor was sealed, a mixed gas of oxygen and nitrogen (oxygen concentration: 4% by volume) was introduced into the vapor phase portion in the reactor to thereby adjust the pressure in the reactor to 5.00 MPa (gauge pressure). Next, the temperature was raised to 95° C. while stirring. The pressure in the reactor was 5.00 MPa (gauge pressure). Then, while continuing to stir, a mixture of cyclohexylamine/N-bromosuccinimide/water/toluene=49.9/0.9/4.9/44.9 (weight ratio) was continuously fed into the reactor at a flow rate of 20 g/hour (retention time 5 hours), and a mixed gas of oxygen and nitrogen (oxygen concentration: 4% by volume) was allowed to flow through the reactor by blowing into a liquid phase of the mixture in the reactor at a flow rate of 20 L/hour to thereby initiate the reaction. While maintaining the pressure in the reactor at 5.00 MPa (gauge pressure), the mixture in the reactor was continuously withdrawn at a flow rate of 20 g/hour through a sintered metal filter made of stainless steel (SUS316), and the reaction was continued at 95° C. for 5 hours while discharging the gas from the vapor phase portion in the reactor via a gas discharge line and then feed of the mixed gas of oxygen and nitrogen was stopped, followed by cooling. The obtained reaction mixture was diluted by the addition of methanol and filtered, and then the obtained filtrate was analyzed. As a result, the conversion ratio of cyclohexylamine was 24.4%, the selectivity to cyclohexanone oxime was 86.3% and the yield of cyclohexanone oxime was 21.1%.

Example 35

In a reactor made of SUS316 (volume: 350 mL) equipped with a thermocouple, a magnetic stirrer, a gas feed line, and a gas discharge line, 9.00 g of the catalyst E obtained in Reference Example 5, 49.9 g (0.50 mol) of cyclohexylamine (manufactured by Wako Pure Chemical Industries, Ltd.), 0.90 g (4.5 mmol) of N-bromosuccinimide (manufactured by Tokyo Chemical Industry Co., Ltd.), 4.90 g (0.27 mol) of water, and 44.9 g of toluene (manufactured by Wako Pure Chemical Industries, Ltd.) were charged and a vapor phase portion in the reactor was replaced by a mixed gas of oxygen and nitrogen (oxygen concentration: 6% by volume). After the reactor was sealed, a mixed gas of oxygen and nitrogen (oxidation concentration: 6% by volume) was introduced into the vapor phase portion in the reactor to thereby adjust the pressure in the reactor to 5.00 MPa (gauge pressure). Next, the temperature was raised to 90° C. while stirring. The pressure in the reactor was 5.00 MPa (gauge pressure). Then, while continuing to stir, a mixture of cyclohexylamine/N-bromosuccinimide/water/toluene=49.9/0.9/4.9/44.9 (weight ratio) was continuously fed into the reactor at a flow rate of 12.5 g/hour (retention time 8 hours), and a mixed gas of oxygen and nitrogen (oxygen concentration: 6% by volume) was allowed to flow through the reactor by blowing into a liquid phase of the mixture in the reactor at a flow rate of 30 L/hour to thereby initiate the reaction. While maintaining the pressure in the reactor at 5.00 MPa (gauge pressure), the mixture in the reactor was continuously withdrawn at a flow rate of 12.5 g/hour through a sintered metal filter made of stainless steel (SUS316), and the reaction was continued at 90° C. for 8 hours while discharging the gas from the vapor phase portion in the reactor via a gas discharge line and then feed of the mixed gas of oxygen and nitrogen was stopped, followed by cooling. The obtained reaction mixture was diluted by the addition of methanol and filtered, and then the obtained filtrate was analyzed. As a result, the conversion ratio of cyclohexylamine was 44.8%, the selectivity to cyclohexanone oxime was 89.3% and the yield of cyclohexanone oxime was 40.0%.

Comparative Example 1

In a reactor made of SUS316 (volume: 200 mL) equipped with a thermocouple, a magnetic stirrer, a gas feed line, and a gas discharge line, 0.30 g of titanium oxide ($TiO_2$, ST-01 manufactured by Ishihara Sangyo Kaisha, Ltd.), 1.52 g (15.3 mmol) of cyclohexylamine (manufactured by Wako Pure Chemical Industries, Ltd.), 0.14 g (0.36 mmol) of 2,2-diphenyl-1-picrylhydrazyl (manufactured by Aldrich), and 7.07 g of acetonitrile (manufactured by Wako Pure Chemical Industries, Ltd.) were charged and a vapor phase portion in the reactor was replaced by a nitrogen gas. After the reactor was sealed, a mixed gas of oxygen and nitrogen (oxygen concentration: 7% by volume) was introduced into the vapor phase portion in the reactor to thereby adjust the pressure in the reactor to 0.90 MPa (gauge pressure). Next, the temperature in the reactor was raised to 80° C. while stirring. The pressure in the reactor was 1.05 MPa (gauge pressure). Then, after keeping the reactor warm at 80° C. for 4 hours while continuing to stir, cooling was performed. The obtained reaction mixture was diluted by the addition of methanol and filtered, and then the obtained filtrate was analyzed. As a result, the conversion ratio of cyclohexylamine was 3.1%, the selectivity to cyclohexanone oxime was 46.3% and the yield of cyclohexanone oxime was 1.4%.

The invention claimed is:

1. A method for producing an oxime having the following formula (II):

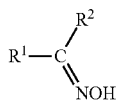

(II)

wherein each of $R^1$ and $R^2$ is independently a hydrogen atom, an optionally substituted hydrocarbon group, or an optionally substituted heterocyclic group, provided that not both $R^1$ and $R^2$ are hydrogen atoms, or
$R^1$ and $R^2$, taken together with the carbon atom to which $R^1$ and $R^2$ are attached, form an optionally substituted alicyclic hydrocarbon group having 3 to 12 carbon atoms,
the method comprising bringing an organic substrate into contact with oxygen in the presence of a catalyst comprising the following compounds (A) and (C):

Compound (A): at least one compound selected from the group consisting of an inorganic peroxo acid, a salt of an inorganic peroxo acid, and an N-halogenated succinimide; and
Compound (C): a layered silicate;
wherein organic substrate is an amine having the following formula (I):

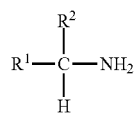

(I)

wherein $R^1$ and $R^2$ are each the same as defined above.

2. A method for producing an amide having the following formula (III):

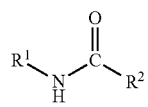

(III)

wherein each of $R^1$ and $R^2$ is independently a hydrogen atom, an optionally substituted hydrocarbon group, or an optionally substituted heterocyclic group, provided that not both $R^1$ and $R^2$ are hydrogen atoms, or
$R^1$ and $R^2$, taken together with the nitrogen atom to which $R^1$ is attached, and the carbon atom to which $R^2$ is attached, form an optionally substituted alicyclic hydrocarbon group having 3 to 12 carbon atoms, the method comprising subjecting the oxime produced by the method according to claim 1 and having the above formula (II) to a Beckmann rearrangement reaction.

3. The method for producing an oxime according to claim 1, wherein the layered silicate is smectite.

4. The method for producing an oxime according to claim 1, wherein the layered silicate contains at least one member selected from the group consisting of hydrogen ion, ammonium ion, quaternary ammonium ions, cations of Group 4 metal elements, cations of Group 5 metal elements, cations of Group 6 metal elements, germanium ions, oxides of positively charged Group 4 metal elements, oxides of positively charged Group 5 metal elements, oxides of positively charged Group 6 metal elements, and positively charged germanium oxides.

5. The method for producing an oxime according to claim 1, wherein the inorganic peroxo acid is at least one compound selected from the group consisting of a peroxomonosulfuric acid and a peroxodisulfuric acid, and the salt of the inorganic peroxo acid is at least one compound selected from the group consisting of a peroxomonosulfate and a peroxodisulfate.

* * * * *